United States Patent
Ohtani et al.

(10) Patent No.: US 6,673,781 B1
(45) Date of Patent: Jan. 6, 2004

(54) TRICYCLIC COMPOUNDS HAVING SPLA$_2$-INHIBITORY ACTIVITIES

(75) Inventors: Mitsuaki Ohtani, Osaka (JP); Masahiro Fuji, Osaka (JP); Tetsuo Okada, Osaka (JP); Makoto Adachi, Osaka (JP); Tomoyuki Ogawa, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 34 days.

(21) Appl. No.: 10/048,348

(22) PCT Filed: Jul. 24, 2000

(86) PCT No.: PCT/JP00/04908

§ 371 (c)(1),
(2), (4) Date: Feb. 1, 2002

(87) PCT Pub. No.: WO01/09130

PCT Pub. Date: Feb. 8, 2001

(30) Foreign Application Priority Data

Aug. 2, 1999 (JP) .............................. 11-218291

(51) Int. Cl.$^7$ .................. C07D 471/04; C07D 471/14; A61K 31/553; A61K 31/5365; A61P 29/00
(52) U.S. Cl. ........................ 514/80; 546/86; 546/87; 546/89; 546/93; 546/94; 546/23; 544/63; 544/234; 544/230.2; 544/232; 514/292; 514/294; 514/248; 514/211.1; 514/215; 540/542; 540/548
(58) Field of Search .................. 546/89, 87, 86, 546/93, 94, 23; 544/63, 234, 232; 514/292, 294, 230.2, 248, 211.1, 215, 80; 540/548, 542

(56) References Cited

FOREIGN PATENT DOCUMENTS

| EP | 0 620 215 A1 | 10/1994 |
|---|---|---|
| EP | 0 675 110 A1 | 10/1995 |
| EP | 1 085 021 A1 | 3/2001 |
| WO | 0 620 214 A1 | 10/1994 |
| WO | WO 96/03120 A1 | 2/1996 |
| WO | WO 96/03376 A1 | 2/1996 |
| WO | WO 96/03383 A1 | 2/1996 |
| WO | WO 97/21664 A1 | 6/1997 |
| WO | WO 97/21716 A1 | 6/1997 |
| WO | WO 98/18464 A1 | 5/1998 |
| WO | WO 98/24437 A1 | 6/1998 |
| WO | WO 98/24756 A1 | 6/1998 |
| WO | WO 98/24794 A1 | 6/1998 |
| WO | WO 98/25609 A1 | 6/1998 |
| WO | WO 95/51605 A1 | 10/1999 |
| WO | WO 99/59999 A1 | 11/1999 |

OTHER PUBLICATIONS

Reynolds et al., "Analysis of Human Synovial Fluid Phospholipase A$^2$ on Short Chain Phosphatidylcholine–Mixed Micelles: Development of a Spectrophotometric Assay Suitable for a Microtiterplate Reader", *Analytical Biochemistry* 204, 190–197 (1992), Academic Press, Inc., California, USA.

Hom et al., "Heterodimeric Bis(amino thiol) Complexes of Oxorhenium(V) That Mimic the Structure of Steroid Hormones. Synthesis and Stereocemical Issues", *J. Org. Chem.* 1996, 61, 2624–2631, American Chemical Society, Illinois, USA.

Anelli et al., "Fast and Selective Oxidation of Primary Alcohols to Aldehydes or to Carboxylic Acids and of Secondary Alcohols to Ketones Mediated by Oxoammonium Salts under Two–Phase Conditions", *J. Org. Chem.* 1987, 52, 2559–2562, American Chemical Society, USA.

Dess et al., "Readily Accessible 12–I–5$^1$ Oxidant for the Conversion of Primary and Secondary Alcohols to Aldehydes and Ketones", *J. Org. Chem.* 1983, 48, 4155–4156, American Chemical Society Illinois, USA.

Mancuso et al., "Oxidation of Long–Chain and Related Alcohols to Carbonyls by Dimethyl Sulfoxide "Activated" by Oxalyl Chloride", *J. Org. Chem.*, vol. 43, No. 12, 1978, pp. 2480–2482, American Chemical Society Pennsylvania, USA.

Corey et al., "Pyridinium Chlorochromate. An Efficient Reagent for Oxidation of Primary and Secondary Alcohols to Carbonyl Compounds", *Tetrahedron Letters*, No. 31, pp. 2647–2650, 1975, Pergamon Press, Massachusetts, USA.

Sasaki et al., "Orientation in the 1,3–Dipolar Cycloaddition Reactions of Heteroaromatic Nitrogen Methlides with Dipolarophiles", *J. Org. Chem.*, vol. 36, No. 6, 1971, pp. 813–818, Japan.

(List continued on next page.)

*Primary Examiner*—Mark L. Berch
*Assistant Examiner*—Kahsay Habte
(74) *Attorney, Agent, or Firm*—Foley & Lardner

(57) ABSTRACT

The present invention provides a compound having sPLA$_2$ inhibiting activity. The compound represented by the formula (I):

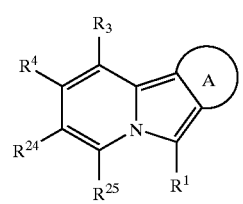

(I)

wherein $R^1$ is (a) C1 to C20 alkyl, C2 to C20 alkenyl, C2 to C20 alkynyl, carbocyclic groups, heterocyclic groups or the like; $R^2$ is $CONH_2$ or $CONHNH_2$; one of $R^3$ and $R^4$ is —($L^2$)-(acidic group) wherein $L^2$ is a group connecting with an acid group and the length of the connecting groups 1 to 5 atoms, and the other is a hydrogen atom; its prodrug, their pharmaceutically acceptable salt, or solvate thereof.

10 Claims, No Drawings

OTHER PUBLICATIONS

Noller et al., "Isobutyl Bromide (Propane, 1–bromo–2–methyl–)", pp. 358–361.

Ha et al., "Selective Bromination of Ketones. A Convenient Synthesis of 5–aminolevulinic Acid", *Synthetic Communications*, 24(18), 2557–2562 (1994), Marcel Dekker, Inc., Korea.

Hagishita et al., "Potent Inhibitors of Secretory Phospholipase A2: Synthesis and Inhibitory Activities of Indolizine and Indene Derivatives", *J. Med Chem.* 1996, 39, 3636–3658, American Chemical Society, USA.

Matsumoto et al., "1,3–Dipolar Cycloaddition Reactions of Cyclooctyne with Pyridinium Dicynomethylides", *J. Heterocyclic Chem.*, 34, 203–208 (1997), Japan.

TRICYCLIC COMPOUNDS HAVING SPLA$_2$-INHIBITORY ACTIVITIES

TECHNICAL FIELD

The present invention relates to a tricyclic compound effective for inhibiting sPLA$_2$-mediated fatty acid release.

BACKGROUND ART sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, cardiac infarction, and so on. The participation of sPLA$_2$ is considered to be extremely wide and, besides, its action is potent.

Examples of sPLA$_2$ inhibitors include compounds described in EP-620214 (JP Laid-Open No. 010838/95, U.S. Pat. No. 5,578,634), EP-620215 (JP Laid-Open No. 025850/95, U.S. Pat. No. 5,684,034), EP-675110 (JP Laid-Open No. 285933/95, U.S. Pat. No. 5,654,326), WO 96/03120 (JP Laid-Open No. 505336/98), WO 96/03376 (JP Laid-Open No. 503208/98, U.S. Pat. No. 5,641,800), WO 96/03383 (JP Laid-Open No. 505584/98), WO 97/21664 (EP-779271), WO 97/21716 (EP-779273), WO 98/18464 (EP839806), WO98/24437(EP846687), WO98/24756, WO98/24794, WO98/25609, WO99/51605, WO99/59999 and the like, or parabromophenacylbromide, mepacrine, manoaride, theilocien A and the like.

DISCLOSURE OF INVENTION

The object of the present invention is to provide tricyclic compounds having sPLA$_2$-inhibitory activities and being useful for treatment of septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, and cardiac infarction.

The present invention relates to I) a compound represented by the formula (I):

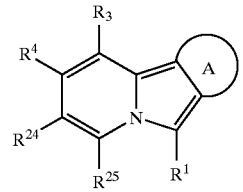

(I)

wherein $R^1$ is a group selected from (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, or (c) —(L$^1$)—R$^5$ wherein L$^1$ is a divalent linking group of 1 to 18 atom(s) selected from hydrogen atom(s), nitrogen atom(s), carbon atom(s), oxygen atom(s), and sulfur atom(s), and R$^5$ is a group selected from the groups (a) and (b);

one of $R^3$ and $R^4$ is —(L$^2$)-(acidic group) wherein L$^2$ is an acid linker having an acid linker length of 1 to 5 and the other is a hydrogen atom;

A ring is a group represented by the formula:

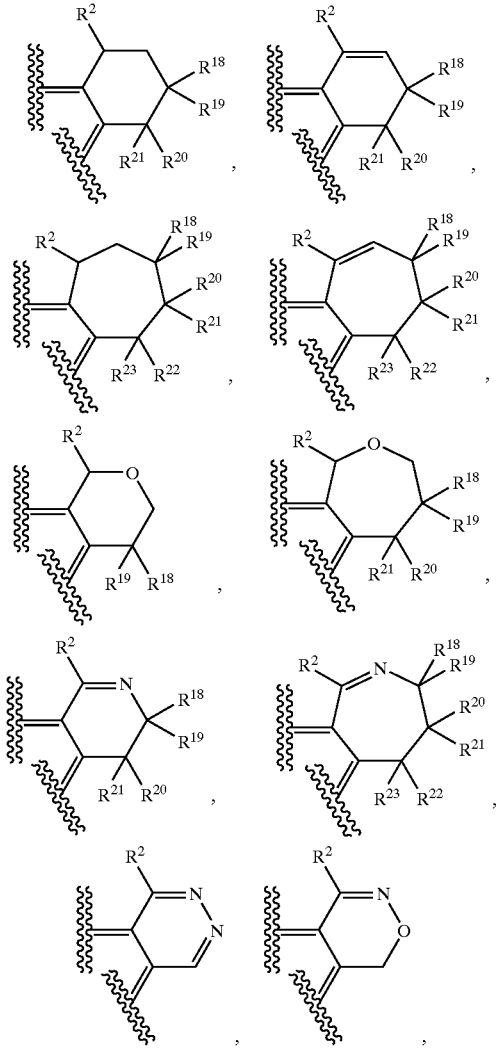

-continued

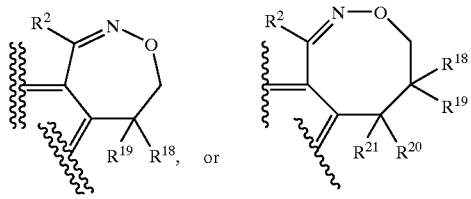

wherein $R^2$ is $CONH_2$ or $CONHNH_2$;
$R^{18}$, $R^{19}$, $R^{20}$, $R^{22}$, and $R^{23}$ are each independently a hydrogen atom, or lower alkyl;
$R^{24}$ and $R^{25}$ are each independently a hydrogen atom, C1 to C6 alkyl, aryl, a halogen or aralkyl;

its prodrug, their pharmaceutically acceptable salt, or hydrate thereof.

In more detail, the present invention relates to II)–XIII).

II) A compound represented by the formula (II):

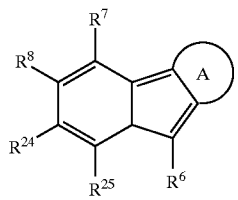

(II)

wherein $R^{24}$, $R^{25}$, and A ring are as defined above;
$R^6$ is —(CH)$_m$—$R^9$ wherein m is an integer from 1 to 6, and $R^9$ is (d) a group represented by the formula:

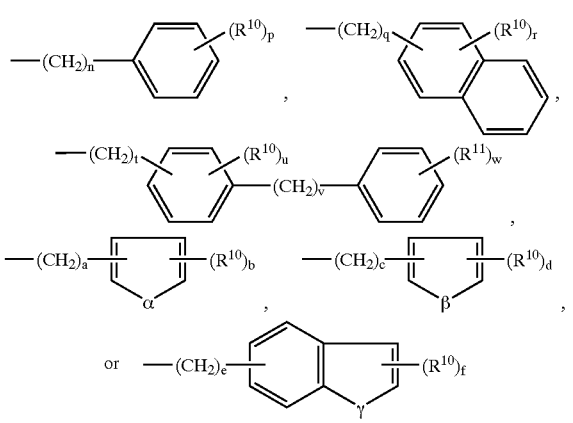

wherein a, c, e, n, q, t and v are each independently an integer from 0 to 2; $R^{10}$ and $R^{11}$ are each independently selected from a halogen, C1 to C10 alkyl, C1 to C10 alkyloxy, C1 to C10 alkylthio, optionally substituted phenyl, optionally substituted heteroaryl and C1 to C10 haloalkyl; α is an oxygen atom or a sulfur atom; β is —CH$_2$— or —(CH$_2$)$_2$—; γ is an oxygen atom or a sulfur atom; b is an integer from 0 to 3, d is an integer from 0 to 4; f, p, and w are each independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen;
one of $R^7$ and $R^8$ is —(L$^3$)—$R^{12}$ wherein $L^3$ is represented by the formula:

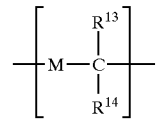

wherein M is —CH$_2$—, —O—, —N(R$^5$)—, or —S—; $R^{13}$ and $R^{14}$ are each independently a hydrogen atom, C1 to C10 alkyl, aryl, aralkyl, carboxy, or a halogen, and $R^{15}$ is a hydrogen atom or C1 to C6 alkyl; and
$R^{12}$ is represented by the formula:

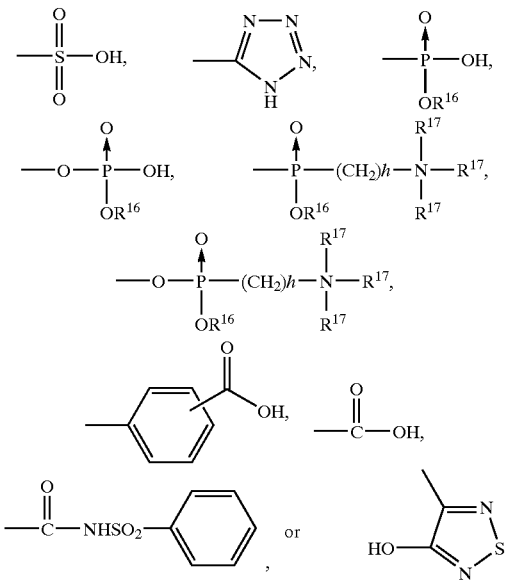

wherein $R^{16}$ is hydrogen atom, a metal, or C1 to C10 alkyl; $R^{17}$ is independently a hydrogen atom or C1 to C10 alkyl; h is an integer from 1 to 8;

its prodrug, their pharmaceutically acceptable salt, or hydrate thereof.

When the above b, d, f, p, r, u, and/or w are 2 or more, a plural number of $R^{10}$ or $R^{11}$ may be different from one another. When $R^{10}$ is a substituent on the naphthyl group, the substituent may substitute at any arbitrary position on the naphthyl group. CH$_2$— and —(CH$_2$)$_2$— in β may be substituted with $R^{10}$.

III) A compound, its prodrug, their pharmaceutically acceptable salt, or hydrate thereof as described in I) or II), wherein said $R^1$ and $R^6$ are represented by the formula:

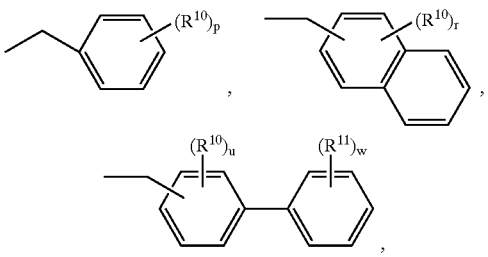

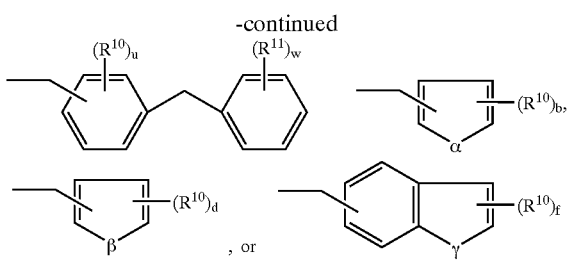

wherein $R^{10}$, $R^{11}$, b, d, f, p, r, u, w, α, β, and γ are as defined above.

When the above b, d, f, p, r, u, and/or w are 2 or more, a plural number of $R^{10}$ or $R^{11}$ may be different from one another. When $R^{10}$ is a substituent on the naphthyl group, the substituent may substitute at any arbitrary position on the naphthyl group. —$CH_2$— and —$(CH_2)_2$— in β may be substituted with $R^{10}$.

IV) A compound, its prodrug, their pharmaceutically acceptable salt, or hydrate thereof as described in any one of I) to III), wherein said $R^1$ and $R^6$ are represented by the formula:

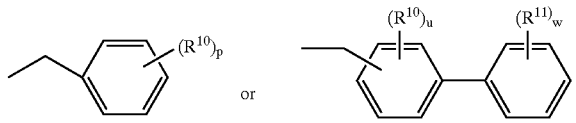

wherein $R^{10}$, $R^{11}$, p, u, and w are as defined above.

When the above p, u, and/or w are 2 or more, a plural number of $R^{10}$ or $R^{11}$ may be different from one another.

V) A compound, its prodrug, their pharmaceutically acceptable salt, or hydrate thereof as described in any one of I) to IV), wherein said $R^3$ and $R^7$ are —O—$(CH_2)_m$—COOH (m is as defined above).

VI) A compound represented by the formula (III):

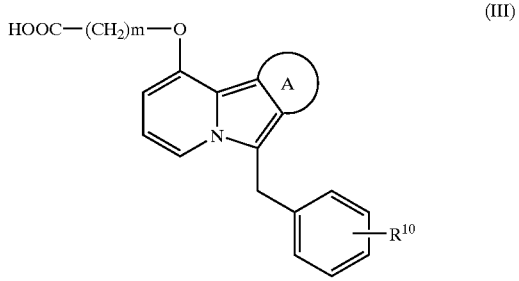

wherein $R^{10}$, A ring, and m are as defined above, its prodrug, their pharmaceutically acceptable salt, or hydrate thereof.

VII) A compound, its prodrug, their pharmaceutically acceptable salt, or hydrate thereof as described in any one of I) to VI), wherein said $R^2$ is —$CONH_2$.

VIII) A compound, its prodrug, their pharmaceutically acceptable salt, or hydrate thereof as described in any one of I) to VII), wherein said $R^{18}$, $R^{19}$, $R^{20}$, $R^{21}$, $R^{22}$, and $R^{23}$ are hydrogen atoms.

IX) A pharmaceutical composition containing a compound as described in any one of I) to VIII) as an active ingredient.

X) A pharmaceutical composition as described in IX), which is for inhibiting $sPLA_2$.

XI) A pharmaceutical composition as described in IX), which is for treatment or prevention of inflammatory diseases.

XII) Use of a compound of any one of I) to VII) for preparation of a pharmaceutical composition for treating inflammatory diseases.

XIII) A method for treating a mammal, including a human, to alleviate the pathological effects of inflammatory diseases, which comprises administration to said mammal of a compound as described in any one of I) to VIII) in a pharmaceutically effective amount.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooctyl); cycloalkenyl (such as cyclobutylenyl, cyclopentenyl, cyclohexenyl, cycloheptenyl, and cyclooctenyl); phenyl, naphthyl, norbornyl, bicycloheptadienyl, indenyl, stilbenyl, terphenylyl, phenylcyclohexenyl, acenaphthyl, anthoryl, biphenylyl, bibenzylyl, and a phenylalkylphenyl derivative represented by the formula:

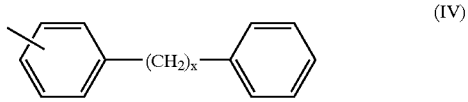

wherein x is an integer from 1 to 8.

The term "heterocyclic group" used in the present specification means a group derived from monocyclic or polycyclic, saturated or unsaturated heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl and the like.

Preferable are thienyl, furyl, thiazolyl, pyridyl as the heterocyclic ring group in the $R^{10}$ and $R^{11}$.

Preferred carbocyclic and heterocyclic groups in $R^1$ are (g) a group represented by the formula:

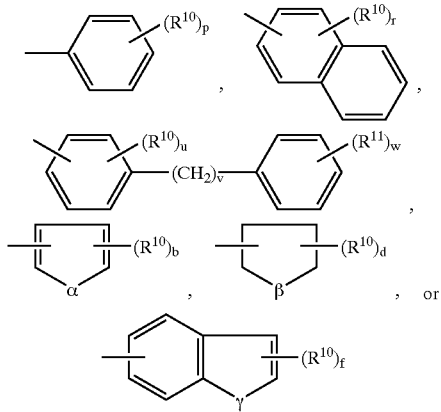

wherein v is an integer from 0 to 2; $R^{10}$ and $R^{11}$ are each independently selected from a halogen, C1 to C10 alkyl, C1 to C10 alkyloxy, C1 to C10 alkylthio, optionally substituted phenyl, optionally substituted heterocyclic group, and C1 to C10 haloalkyl, α is an oxygen atom or a sulfur atom, β is —CH$_2$— or —(CH$_2$)$_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4. When the above b, d, f, p, r, u, and/or w are 2 or more, a plural number of $R^{10}$ or $R^{11}$ may be different from one another. When $R^{10}$ is a substituent on the naphthyl group, the substituent may be substituted at any arbitrary position on the naphthyl group. —CH$_2$— and —(CH$_2$)$_2$— in β may be substituted with $R^{10}$.

A more preferable example includes (h) a group represented by the formula:

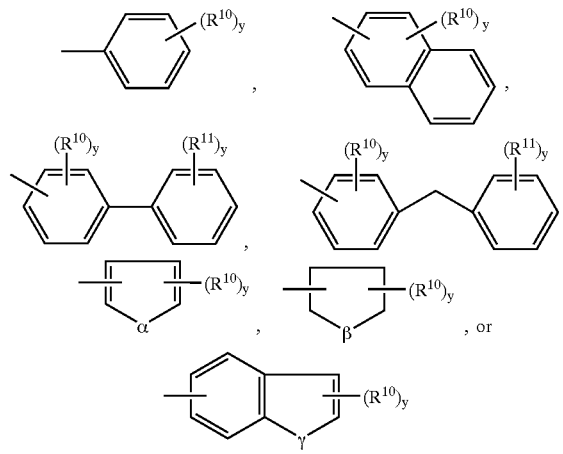

wherein $R^{10}$, $R^{11}$, α, β, and γ are the same as defined above, and y is independently 0 or 1. When $R^{10}$ is a substituent on the naphthyl group, the substituent may be substituted at any arbitrary position on the naphthyl group. —CH$_2$— and —(CH$_2$)$_2$— in β may be substituted with $R^{10}$.

The term "non-interfering substituent" in the present specification means a group suitable for substitution of group (a) (e.g., "alkyl", "alkenyl" "carbocyclic group" and "heterocyclic group") in $R^1$ on tricyclic compound represented by the formula (I). An example of the non-interfering substituents includes C1 to C10 alkyl, C2 to C6 alkenyl, C2 to C6 alkynyl, C7 to C12 aralkyl (such as benzyl and phenethyl), C7 to C12 alkaryl, C3 to C8 cycloalkyl, C3 to C8 cycloalkenyl, phenyl, tolyl, xylyl, biphenylyl, C1 to C10 alkyloxy, C1 to C6 alkyloxy C1 to C6 alkyl (such as methyloxymethyl, ethyloxymethyl, methyloxyethyl, and ethyloxyethyl), C1 to C6 alkyloxy C1 to C6 alkyloxy (such as methyloxymethyloxy and methyloxyethyloxy), C1 to C6 alkylcarbonyl (such as methylcarbonyl and ethylcarbonyl), C1 to C6 alkylcarbonylamino (such as methylcarbonylamino and ethylcarbonylamino), C1 to C6 alkyloxyamino (such as methyloxyamino and ethyloxyamino), C1 to C6 alkyloxyaminocarbonyl (such as methyloxyaminocarbonyl and ethyloxyaminocarbonyl), mono or di C1 to C6 alkylamino (such as methylamino, ethylamino, dimethylamino, and ethylmethylamino), C1 to C10 alkylthio, C1 to C6 alkylthiocarbonyl (such as methylthiocarbonyl and ethylthiocarbonyl), C1 to C6 alkylsulfinyl (such as methylsulfinyl and ethylsulfinyl), C1 to C6 alkylsulfonyl (such as methylsulfonyl and ethylsulfonyl), C2 to C6 haloalkyloxy (such as 2-chloroethyloxy and 2-bromoethyloxy), C1 to C6 haloalkylsulfonyl (such as chloromethylsulfonyl and bromomethylsulfonyl), C1 to C10 haloalkyl, C1 to C6 hydroxyalkyl (such as hydroxymethyl and hydroxyethyl), C1–C6 alkyloxycarbonyl (such as methyloxycarbonyl and ethyloxycarbonyl), —(CH$_2$)z—O—(C1 to C6 alkyl), benzyloxy, aryloxy (such as phenyloxy), arylthio (such as phenylthio), —(CONHSO$_2$R$^{20}$), formyl, amino, amidino, halogen, carbamyl, carboxyl, carbalkyloxy, —(CH$_2$)z—COOH (such as carboxymethyl, carboxyethyl, and carboxypropyl), cyano, cyanoguanidino, guanidino, hydrazido, hydrazino, hydroxy, hydroxyamino, nitro, phosphono, —SO$_3$H, thioacetal, thiocarbonyl, carbonyl, carbocyclic groups, heterocyclic groups and the like, wherein z is an integer from 1 to 8 and $R^{20}$ is C1 to C6 alkyl or aryl.

Preferable are halogens, C1 to C6 alkyl, C1 to C6 alkyloxy, C1 to C6 alkylthio, and C1 to C6 haloalkyl as the "non-interfering substituent" in the $R^1$. More preferable are halogens, C1 to C3 alkyl, C1 to C3 alkyloxy, C1 to C3 alkylthio, and C1 to C3 haloalkyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a tricyclic nucleus through a suitable linking atom (hereinafter defined as "acid linker"). An example of the acidic group includes (k) a group represented by the formula:

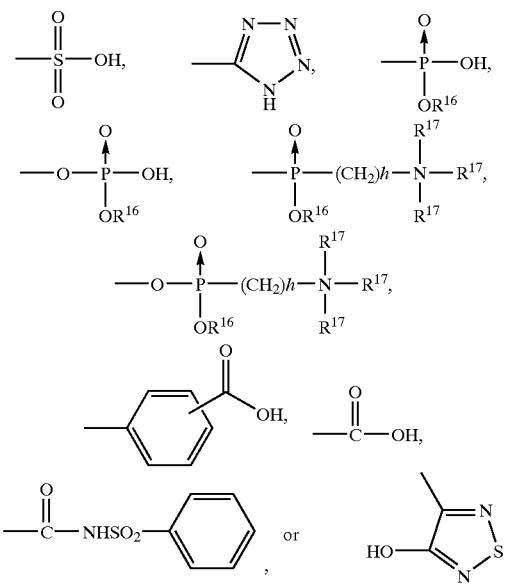

wherein $R^{16}$ is a hydrogen atom, a metal, or C1 to C10 alkyl; each $R^{17}$ is independently a hydrogen atom or C1 to C10 alkyl; h is an integer from 1 to 8. Preferable is (1) —COOH, —SO$_3$H, or P(O)(OH)$_2$. More preferable is (m) —COOH. And preferable is also their ester and prodrug.

The term "acid linker" in the present specification means a divalent linking group represented by a symbol —(L$^2$)—, and it functions to join tricyclic nucleus to an "acidic group" in the general relationship. An example of it includes (n) a group represented by the formula:

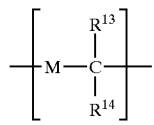

wherein M is —CH$_2$—, —O—, —N(R$^{15}$)—, or —S—, and $R^{13}$ and $R^{14}$ are each independently a hydrogen atom, C1 to C10 alkyl, aryl, aralkyl, carboxy, or halogens, wherein $R^{15}$ is a hydrogen atom or C1–C6 alkyl. Preferable are (o) —O—CH$_2$—, —S—CH$_2$—, —N(R$^{15}$)—CH$_2$—, —CH$_2$—CH$_2$—, —O—CH(CH$_3$)—, or —O—CH((CH$_2$)$_2$Ph)— wherein $R^{15}$ is C1 to C6 alkyl and Ph is phenyl. More preferable is (p) —O—CH$_2$— or —S—CH$_2$—.

In the present specification, the term "acid linker length" means the number of atoms (except for hydrogen atoms) in the shortest chain of a linking group —(L$^2$)— which connects tricyclic nucleus with the "acidic group". The presence of a carbocyclic ring in —(L$^2$)— counts as the number of atoms approximately equivalent to the calculated diameter of the carbocyclic ring. Thus, a benzene and cyclohexane ring in the acid linker counts as two atoms in culculating the length of —(L$^2$)—. A preferable length is 2 to 3.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy, at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl (such as 3-phenylpropyl), naphthylmethyl (such as 1-naphtbylmethyl) and the like.

The term "alkyloxycarbonyl" in the present specification means C1–C6 alkyloxycarbonyl. An example of the alkyloxycarbonyl includes methyloxycarbonyl, ethyloxycarbonyl, n-propyloxycarbonyl and the like.

The term "acyl" in the present specification means C1–C6 alkylcarbonyl or arylcarbonyl opptionally substituted with a halogen and the like. An example of the acyl includes acetyl, trifluoroacetyl, propionyl, benzoyl and the like.

In the present specification, preferable are a halogen, C1–C10 alkyl, C1–C10 alkyloxy, C1–C10 alkylthio, and C1–C10 haloalkyl and the like as substituents for "optionally substituted phenyl" and" "optionally substituted heterocyclic group". These substituents may be substituted with one or more positions.

A group of preferable substituents as the $R^1$ to $R^3$ of the compound represented by the formula (I) will be shown in items (A) to (O). Preferable are hydrogen atoms as the $R^4$, $R^{18}$, $R^{19}$, $R^{20}$, $R^{21}$, $R^{22}$, $R^{23}$, $R^{24}$, and $R^{25}$. Items (f) to (p) are the same group as described above.

As the $R^1$, (A): —(L$^1$)—R$^5$, (B): —(CH$_2$)$_{1-2}$-(f), (C): —(CH$_2$)$_{1-2}$-(g), and (D): —(CH$_2$)$_{1-2}$-(h) are preferred.

As the $R^2$, (E): CONH$_2$ or CONHNH$_2$, and (F): CONH$_2$ are preferred.

As the $R^3$, (G): -(n)-(k), (H): -(n)-(l), (I): -(n)-(m), (J): -(o)-(k), (K): -(o)-(l), (L): -(o)-(m), (M): -(p)-(k), (N): -(p)-(l), and (O): -(p)-(m) are preferred.

A preferred group of compounds represented by the formula (I) is shown below.

($R^1$,$R^2$,$R^3$)=(A,E,G), (A,E,H), (A,E,I), (A,E,J), (A,E,K), (A,E,L), (A,E,M), (A,E,N), (A,E,O), (A,F,G), (A,F,H), (A,F,I), (A,F,J), (A,F,K), (A,F,L), (A,F,M), (A,F,N), (A,F,O), (B,E,G), (B,E,H), (B,E,I), (B,E,J), (B,E,K), (B,E,L), (B,E,M), (B,E,N), (B,E,O), (B,F,G), (B,F,H), (B,F,I), (B,F,J), (B,F,K), (B,F,L), (B,F,M), (B,F,N), (B,F,O), (C,E,G), (C,E,H), (C,E,I), (C,E,J), (C,E,K), (C,E,L), (C,E,M), (C,E,N), (C,E,O), (C,F,G), (C,F,H), (C,F,I), (C,F,J), (C,F,K), (C,F,L), (C,F,M), (C,F,N), (C,F,O), (D,E,G), (D,E,H), (D,E,I), (D,E,J), (D,E,K), (D,E,L), (D,E,M), (D,E,N), (D,E,O), (D,F,G), (D,F,H), (D,F,I), (D,F,J), (D,F,K), (D,F,L), (D,F,M), (D,F,N), and (D,F,O).

BEST MODE FOR CARRYING OUT THE INVENTION

The compounds of the invention represented by the formula (I) can be synthesized in accordance with well-known method described in chemical journals. The compounds of the invention represented by the formula (I) can also be synthesized in accordance with the following methods A to E. Although representative methods are exemplified, enlarged rings can also be synthesized in a similar manner.

(Method A)

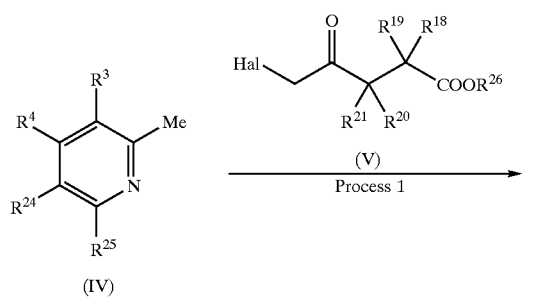

(IV)    (V)    Process 1

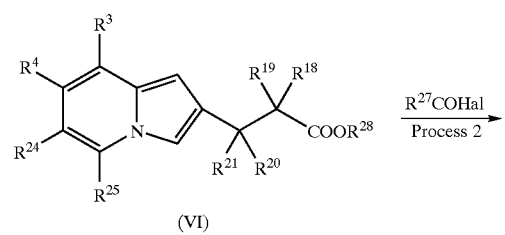

(VI)    Process 2    $R^{27}$COHal

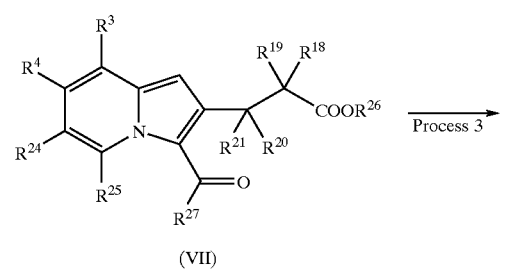

(VII)    Process 3

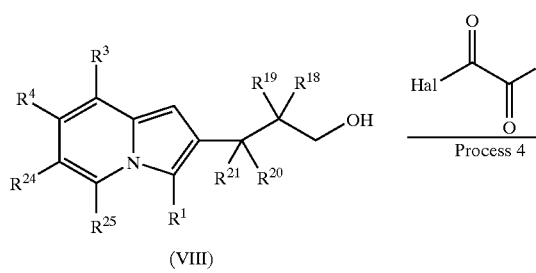

(VIII)    Process 4

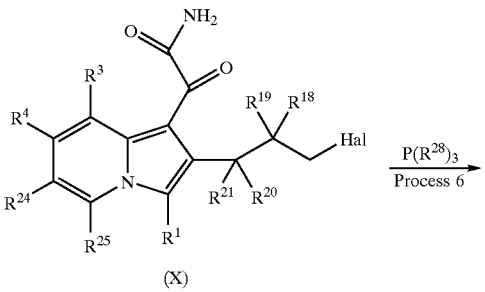

(IX)    Process 5

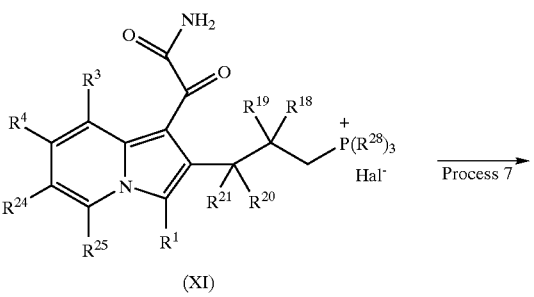

(X)    Process 6    $P(R^{28})_3$ (XI)    Process 7

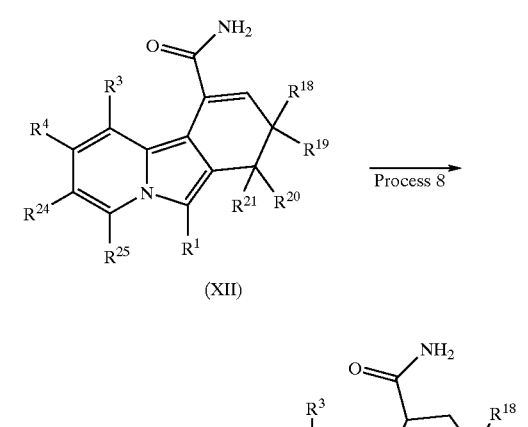

(XII)    Process 8

(XIII)

wherein $R^1$, $R^3$, $R^4$, $R^5$, $R^{18}$, $R^{19}$, $R^{20}$, $R^{21}$, $R^{24}$, and $R^{25}$ are as defined above, $R^{26}$ is lower alkyl, $R^{27}$CO— is a precursor of $R^1$, $R^{28}$ is optionally substituted aryl, Hal are independently a halogen.

(Process 1)

A mixture of the compound (IV) and the compound (V) is stirred at 40° C. to 90° C., preferably 50 to 70° C. for 3 to 36 h, preferably 12 to 24 h to give the quaternary salt. To a solution of the obtained quaternary salt in a solvent such as 1,2-dichloroethane or acetonitrile is added a base such as 1,8-diazabicyclo[5.4.0]-7-undecene (DBU) or triethylamine, and the resulting mixture is stirred at 40° C. to 90° C., preferably 50 to 70° C. for 3 to 36 h, preferably 12 to 24 h. After the reaction mixture is subjected to a usual work-up, the compound (VII) can be obtained.

The compound (IV) is commercial available or can be synthesized in accordance with the method described in J.

Med. Chem., 3636–58(1996). The compound (V) can be synthesized in accordance with the method described in Synth. Commun. 24, 2557 (1994).

(Process 2)

The present process is performed by Friedel-Crafts reaction. To a solution of the compound (VI) in a solvent such as 1,2-dichloroethane or dichloromethane are slowly added $R^{27}COHal$ and a Lewis acid such as $AlCl_3$, $SbF_5$, or $BF_3$ at −78° C. to 10° C., preferably −20° C. to ice bath, and the reaction mixture is stirred at −10° C. to 10° C., preferably 0° C. to 10° C. for 5 to 30 min, preferably 10 to 20 min. This reaction can be performed without solvent by dissolving the compound (VI) in $R^{27}COHal$ and in accordance with the above-mentioned procedure. After the reaction mixture is subjected to a usual work-up, the compound (VII) can be obtained (Ref: J. Med. Chem., 39, 3636–58(1996)).

(Process 3)

The present process includes the reduction of an ester group of a side chain at 2-position and a carbonyl group of 3-position at the same time. To a solution of the compound (VII) in a solvent such as tetrahydrofuran or dichloromethane are added a reducing agent (e.g., a mixed agent of sodium borohydride and a Lewis acid such as aluminum chloride), and the mixture is reacted at 20° C. to 100° C., preferably 20° C. to 50° C. for 1 to 5 h, preferably 1 to 3 h to obtain the compound (VIII).

(Process 4)

To a solution of the compound (VIII) in a solvent such as 1,2-dichloroethane or tetrahydrofuran are added Hal—C(=O)—C(=O)—Hal (e.g., oxalyl chloride) and a base such as N-methylmorpholine or triethylamine, and the mixture is stirred at 30 to 70° C., preferably 40 to 60° C. for 1 to 10 h, preferably, 3 to 6 h. The reaction mixture is poured into a cold aqueous ammonium solution and the resulting mixture is stirred for 5 to 30 min, preferably, 10 to 20 min. After the reaction mixture is subjected to a usual work-up, the compound (IX) can be obtained.

(Process 5)

The present process includes the conversion of a hydroxy group to halogen. To a solution of the compound (IX) is added triphenylphosphine and N-bromosuccinimide, and the mixture is reacted at 0° C. to 50° C., preferably 0° C. to 20° C. for 1 to 10 h, preferably for 1 to 5 h to obtain the compound (X). It can be synthesized by using phosphorous tribroimde in accordance with the method described in Org. Synth Coll. Vol. 2, p-358, or by using triphenylphosphine and bromine in accordance with the method described in J. Am. Chem. Soc., 107, 5238 (1995).

(Process 6)

The present process includes the preparation of the phosphonium salt. A mixture of the compound (X) and triphenylphosphine in a solvent such as acetonitrile or toluene is reacted at 80 to 150° C., preferably 100 to 120° C. for 5 to 72 h, preferably 10 to 24 h to obtain the compound (XI).

(Process 7)

The present process is for constructing a ring by Wittig reaction. To a solution of the compound (XI) in a solvent such as acetonitrile, or tetrahydrofuran is added a base such as 1,8-dizabicyclo[5.4.0]-7-undecene (DBU), potassium t-butoxide, and the mixture is reacted at 20° C. to 120° C., preferably 80° C. to 100° C. for 3 to 24 h, preferably 5 to 10 h to obtain the compound (XII).

(Process 8)

The present process includes the reduction of the double bond by hydrogenation. To a solution of the compound (XII) in a solvent such as tetrahydrofuran, methanol or ethyl acetate is added a catalyst such as Palladium-Carbon, and the mixture is reacted under hydrogen atmosphere at room temperature for 1 to 5h, preferably 1 to 2 h to yield the compound (XIII).

(Method B)

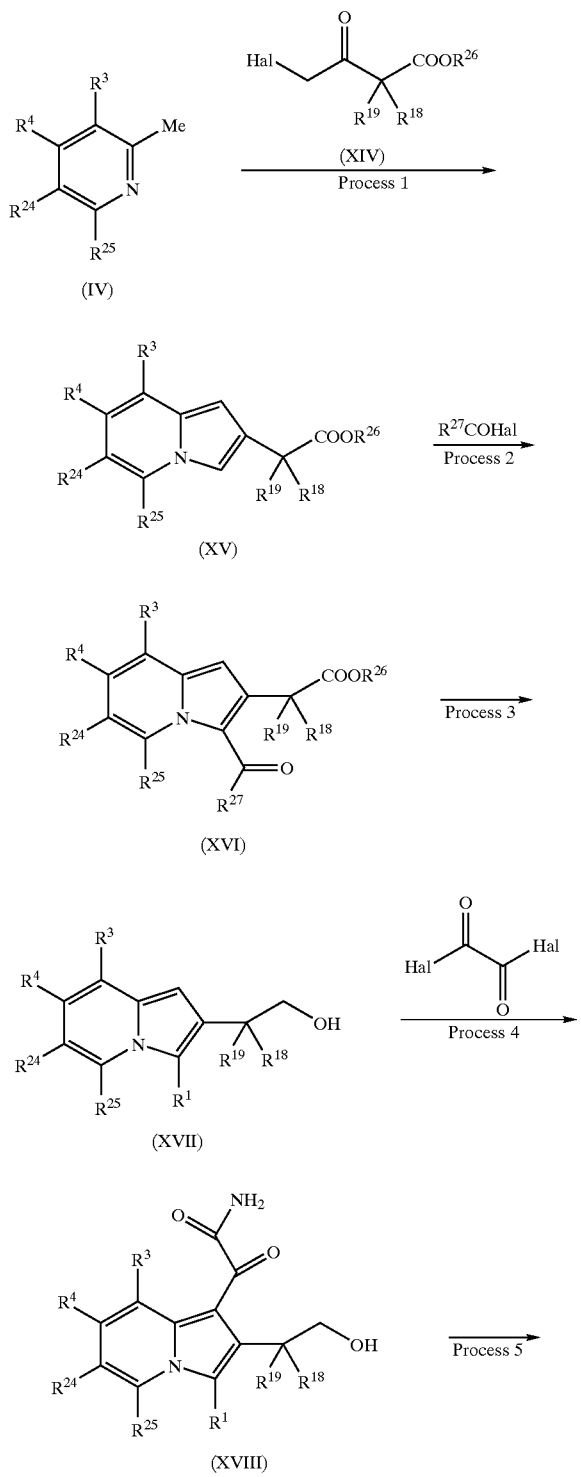

-continued

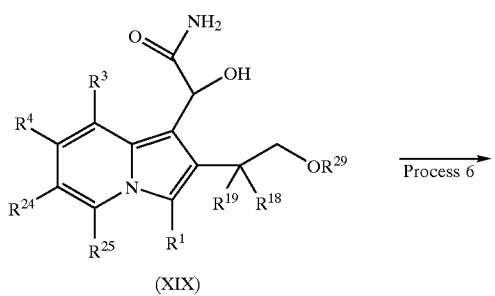

(XIX)

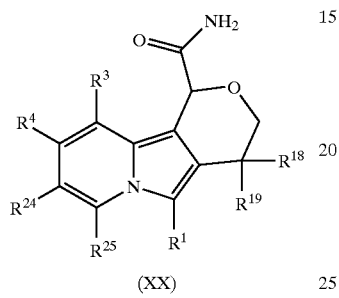

(XX)

wherein $R^1$, $R^3$, $R^4$, $R^5$, $R^{18}$, $R^{19}$, $R^{24}$, $R^{25}$, $R^{26}$, $R^{27}$, and Hal are as defined above. $R^{29}$ is a methanesulfonyl group, p-toluenesulfonyl or the like.

(Process 1)

The present process may be carried out in accordance with the same procedure as that of the Method A—Process 1.

(Process 2)

The present process may be carried out in accordance with the same procedure as that of the Method A—Process 2.

(Process 3)

The present process may be carried out in accordance with the same procedure as that of the Method A—Process 3.

(Process 4)

The present process may be carried out in accordance with the same procedure as that of the Method A—Process 4.

(Process 5)

The present process is for the conversion of a hydroxy group at 2-position to a good leaving group followed by the reduction of a carbonyl group of a side chain at 1-position. A solution of the compound (XVIII) in a solvent such as dichloromethane or the like is reacted with $R^{29}$—Cl in the presence of a base such as triethylamine or the like at 0° C. to 80° C., preferably 0° C. to 20° C. for 1 to 5 h, preferably 1 to 2 h. A solution of the obtained compound in a solvent such as tetrahydrofuran is reacted with a reductant such as sodium borohydride at 0° C. to 80° C., preferably 0° C. to 20° C. for 1 to 5 h, preferably 1 to 2 h to give the compound (XIX).

(Process 6)

The present step is for constructing a ring. To a solution of the compound (XIX) in a solvent such as tetrahydrofuran, or dimethylformamide is added a base such as sodium hydride, or potassium tert-butoxide at 0 to 100° C., preferably 20 to 50° C. for 1 to 8 h, preferably 1 to 3 h to give the compound (XX).

(Method C)

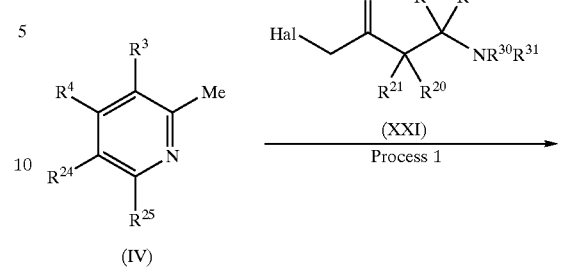

(IV)

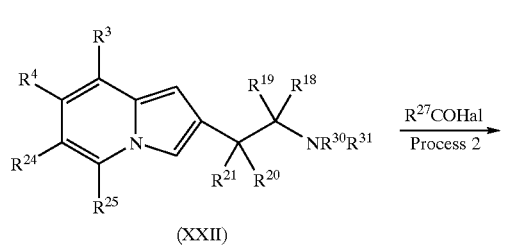

(XXII)

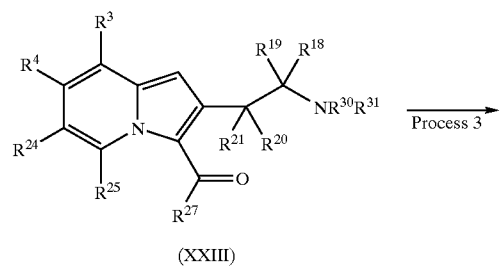

(XXIII)

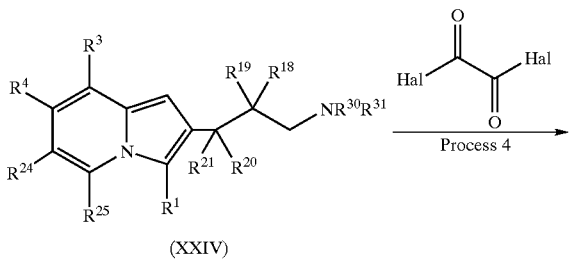

(XXIV)

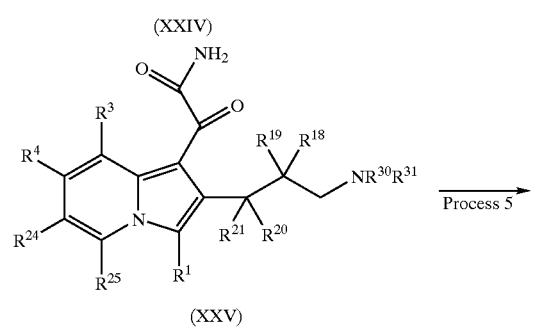

(XXV)

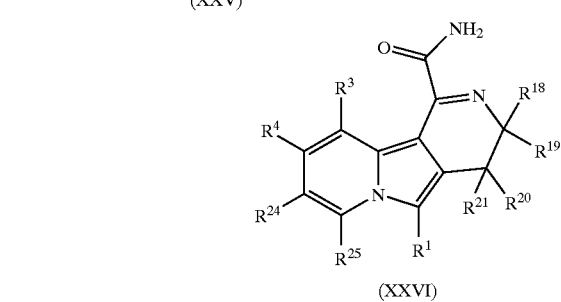

(XXVI)

wherein $R^1$, $R^3$, $R^4$, $R^5$, $R^{18}$, $R^{19}R^{20}$, $R^{21}$, $R^{24}$, $R^{25}$, $R^{27}$, and Hal are as defined above, one of $R^{30}$ and $R^{31}$ is a hydrogen atom, the other is a protecting group of an amino group.

(Process 1)

The present process may be carried out in accordance with the same procedure as that of the Method A—Process 1.

(Process 2)

The present process may be carried out in accordance with the same procedure as that of the Method A—Process 2.

(Process 3)

The present process is for the reduction of a carbonyl group at 3-position methylene. To a solution of Lewis acid (e.g., $AlCl_3$ or the like) in a solvent such as dichloromethane or tetrahydrofuran is slowly added a reducing agent such as borane-tert-butylamine complex or sodium borohydride at −20° C. to 10° C., preferably in an ice bath, and the reaction mixture is stirred for 5 to 30 min, preferably 10 to 20 min. To the resulting reaction mixture is added a solution of the compound (XXIII) in a solvent such as dichloromethane or tetrahydrofuran at −20° C. to 10° C. preferably in an ice bath and the mixture is stirred for 20 to 30 min, and then at 15° C. to 40° C., preferably 20 to 30° C. for 1 to 5 h, preferably 2 to 3 h. After a usual work-up, the compound (XXIV) can be obtained (Ref: J. Med. Chem., 39, 3636–58 (1996)).

(Process 4)

The present process may be carried out in accordance with the same procedure as that of the Method A—Process 4.

(Process 5)

The present process is for the deprotection of the protecting group of an amino group and the construction of the ring. To a solution of the compound (XXV) in a solvent such as dichloromethane or the like is added an acid such as trifluoroacetic acid and the mixture is reacted at 0° C. to 80° C., preferably 20° C. to 50° C. for 1 to 20 h, preferably 3 to 8 h to give the compound (XXVI).

(Method D)

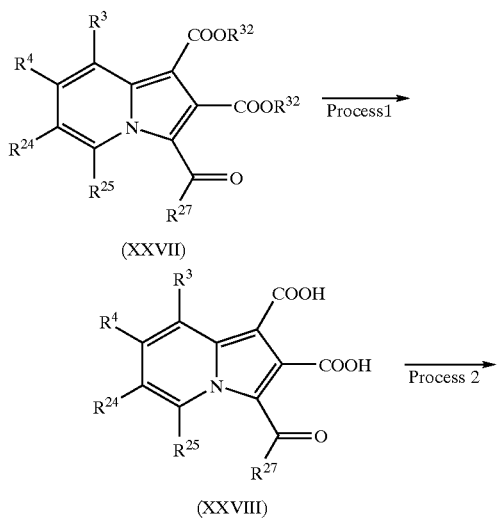

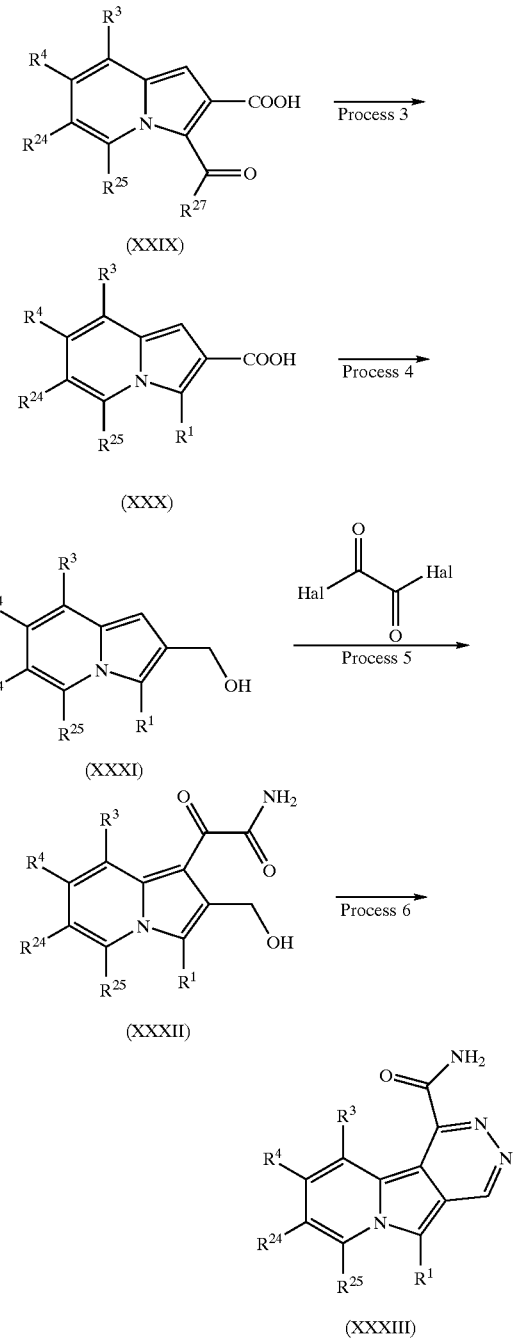

wherein $R^1$, $R^3$, $R^4$, $R^{24}$, $R^{25}$, $R^{27}$, and Hal are as defined above, $R^{32}$ is lower alkyl.

(Process 1)

The present process is for hydrolysis of ester. The compound (XXVII) can be synthesized in accordance with the method described in J. Org. Chem., 36, 813 (1971). To a solution of the compound (XXVII) in a solvent such as tetrahydrofuran, ethanol, or dimethylsulfoxide is added a base such as sodium hydroxide, potassium hydroxide at 20 to 150° C., preferably 50 to 150° C. for 1 to 10 h, preferably 3 to 5 h to obtain the compound (XXVIII).

(Process 2)

The present process is for the decarboxylation. A solution of the compound (XXVIII) in solvent such as dimethyl sulfoxide or dimethylformamide is reacted at 50 to 200° C., preferably 100 to 150° C. for 1 to 5 h, preferably 1 to 2 h.
(Process 3)

The present process may be carried out in accordance with the same procedure as that of the Method C—Process 3.

(Process 4)

The present process is the reduction of carboxylic acid. Diborane, sodium borohydride-aluminum chloride, diisobutylaluminum hydride, lithium aluminum hydride and the like can be used as a reducing agent. In case of using lithium aluminum hydride, to a solution of the compound (XXX) in tetrahydrofuran or diethyl ether is added lithium aluminum hydride at 0° C. to 100° C., preferably 20° C. to 50° C. for 1 to 5 h, preferably 1 to 2 to give the compound (XXXI).

(Process 5)

The present process may be carried out in accordance with the same procedure as that of the Method A—Process 4.

(Process 6)

The present process is for the oxidation of a hydroxy group and the construction of the pyridazine ring.

The present process can be performed by usual oxidation and the following four types of oxidation are preferable.

i) PCC Oxidation (To a solution of the compound (XXXII) in a solvent such as dichloromethane or the like is added pyridinium chlorochromate (PCC) and the mixture is reacted at −20 to 60° C., preferably 0 to 40° C. for 1 to 30 h, preferably 3 to 20 h to yield the aimed oxidant.)(Ref: Tetrahedron Lett., 2647–2650 (1975))

ii) Swern Oxidation (Dichloromethane is cooled at −78° C., and to the solution are added successively oxalyl chloride, dimethyl sulfoxide, and the compound (XXXII). The mixture is warmed to −45° C. to 0° C., and reacted for 1 to 30 h, preferably 1 to 10 h and then is subjected to usual work-up to give the desired compound.) (Ref: J. Org. Chem., 43, 2480–2482 (1978))

iii) Dess-Martin Oxidation (The oxidation can be carried out in solution such as tetrahydrofuran or the like by reacting Dess-Martin reagent in dimethyl sulfoxide.) (Ref: J. Org. Chem., 48, 4155–4156 (1983))

iv) Oxidation with a halogeno oxoacid (The compound (XXXII) is reacted in the presence of 2,2,6,6-tetramethylpiperidine-1-oxyl (TEMPO) with an oxidizing agent such as a halogeno oxoacid or the like in accordance with the method described in J. Org. Chem., 52, 2559–2562 (1987) to give the product. 2,2,6,6-tetramethylpiperidine-1-oxyl, 4-methoxy-2,2,6,6-tetramethylpiperidine-1-oxyl, 4-acetylamino-2,2,6,6-tetramethylpiperidine-1-oxyl, 4-benzoyloxy-2,2,6,6-tetramethylpiperidine-1-oxyl, 4-cyano-2,2,6,6-tetramethylpiperidine-1-oxyl or like the can be used as TEMPO or the like. Sodium hypochlorite, sodium hypobromite, sodium bromide, high test hypochlorite or the like can be used as a halogeno oxoacid. Ethyl acetate, acetonitrile, and dichlormethane can be used as a solvent.

Ring closing reaction can be carried out by reacting the obtained compound with hydrazine hydrate ($NH_2NH_2H_2O$) in a solvent such as ethanol or the like at 0° C. to 100° C., preferably 0° C. to 30° C. for 1 to 10 h, preferably 2 to 3 h.)

(Method E)

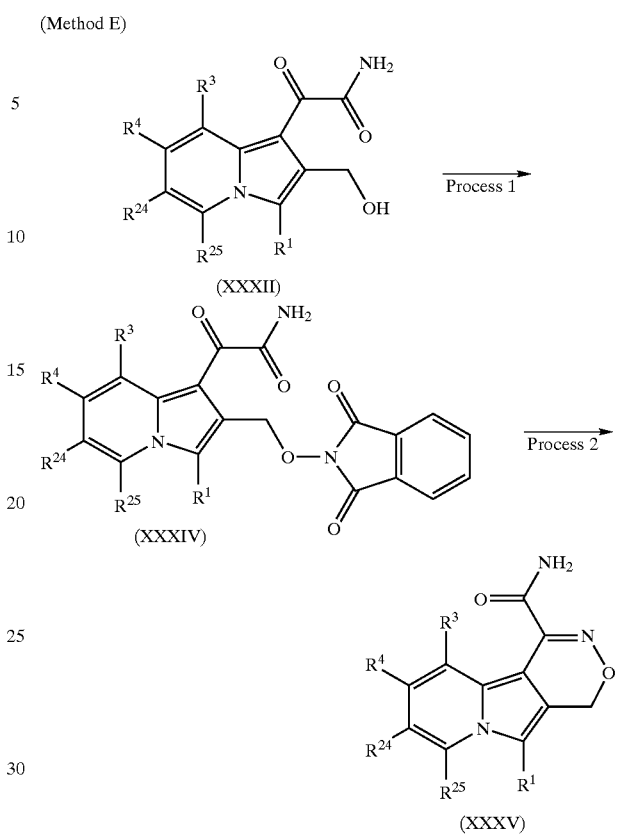

wherein $R^1$, $R^3$, $R^4$, $R^{24}$, and $R^{25}$ are as defined above.

(Process 1)

The present process is for the preparation of N-alkoxyphthalimide by Mitsunobu-reaction. The compound (XXXII) in a solvent such as tetrahydrofuran or the like is reacted with triphenylphosphine, N-hydroxyphthalimide, diethyl azodicarboxylate, and the like at 0 to 80° C., preferably 10 to 30° C. for 1 to 5 h, preferably 1 to 2 h to obtain the compound (XXXIV).

(Process 2)

The present process is for the ring formation. The compound (XXXIV) in a solvent such as dichloromethane or the like is reacted with reagents such as hydrazine, N-methylhydrazine or the like at 0° C. to 80° C., preferably 10° C. to 30° C. for 1 to 5 h, preferably 1 to 2 h to give the compound (XXXV).

Where a compound of the present invention has an acidic or basic functional group, a variety of salts having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts".

(e.g., S. M. Berge et al., "Pharmaceutical Salts, "J. Phar. Sci., 66, 1–19 (1977)). Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like. In case of forming a hydrate, a questioned compound may be coordinated with a suitable number of water molecules.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. More preferable is C1–C6 alkyl ester of acidic group (e.g., methyl ester, ethyl ester). Double ester such as (acyloxy)alkyl ester or ((alkyloxycarbonyl)oxy)alkyl ester type prodrugs may be optionally manufactured.

The term "inhibit" means that release of fatty acid started by $sPLA_2$ decreases significantly by the compounds:of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit $sPLA_2$ inhibiting activity as per the description of the experimental examples which will be described hereinafter. Accordingly, when a curatively effective amount of the compounds represented by the formulae (I), (II), and (III), the prodrug derivatives thereof, or their pharmaceutically acceptable salts, or their hydrate is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, psoriasis, cardiac failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The dosage varies with the conditions of the disease, administration route, age and body weight of patient. In the case of oral administration, the dosage can generally be between 0.01 to 50 mg/kg/day for adult.

The following examples are provided to further illustrate the present invention and are not to be constructed as limiting the scope thereof.

Abbreviations described below are used in the following examples.

Me:methyl
Et:ethyl
Ph:phenyl
Bn:benzyl
DBU:1,8-diazabicyclo[5.4.0]-7-undecene

EXAMPLE

Example 1

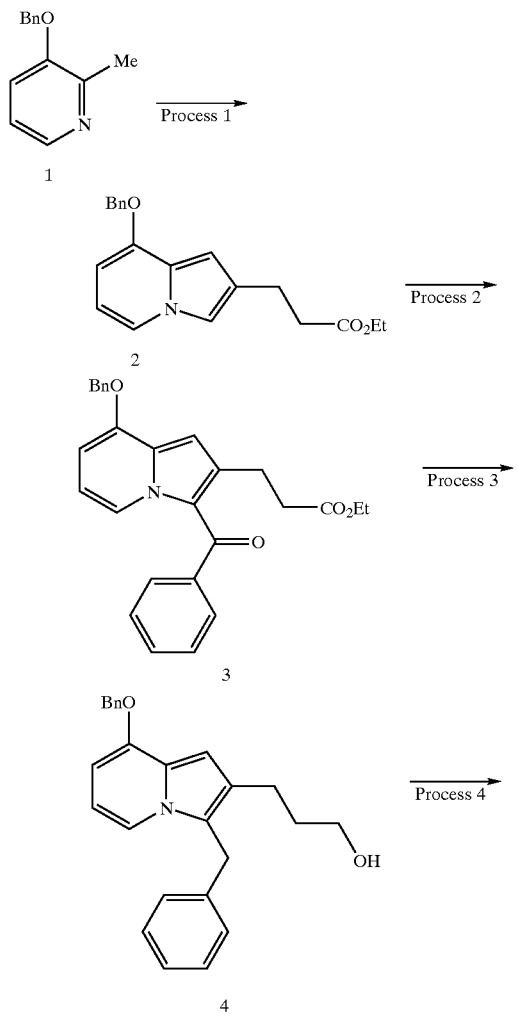

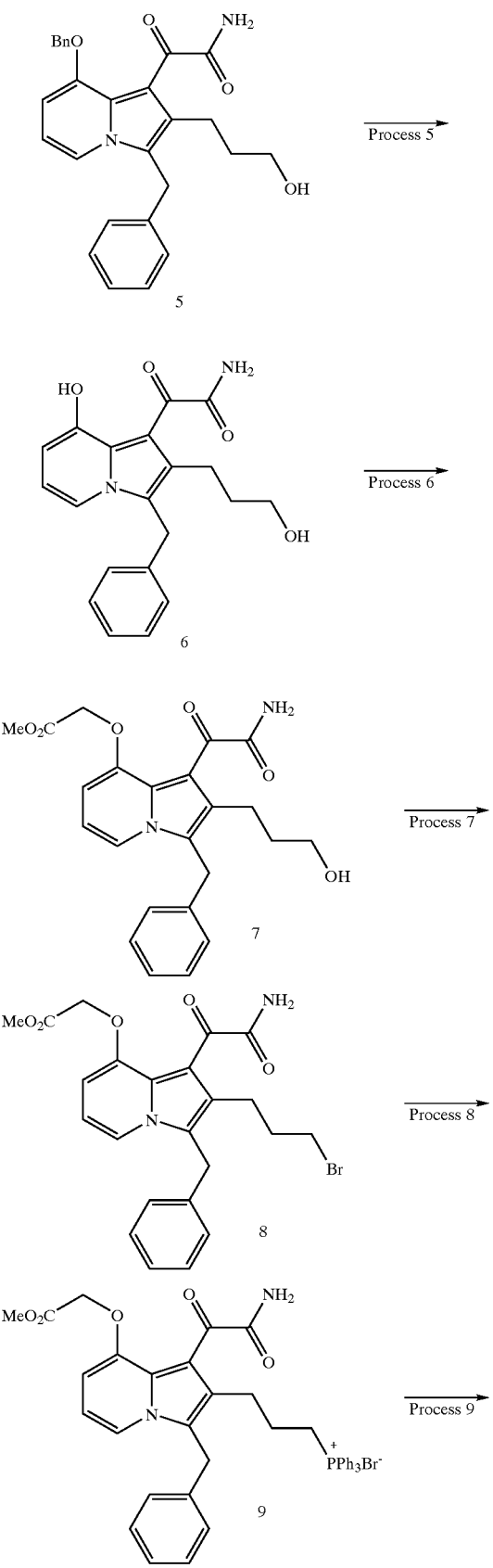

-continued

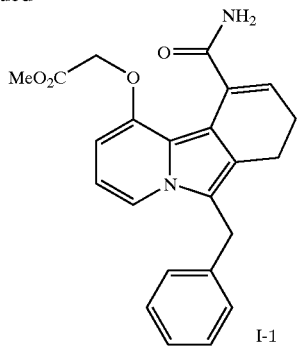

I-1

Example 1
Process 1

A mixture of the compound (1) 8.90 g (44 mmol) and ethyl 5-bromo-4-oxopentanate 10.20 g (45 mmol) was stirred at 60° C. for 1 h. After the reaction mixture was diluted with toluene, DBU 7.6 ml (50 mmol) was added and the resulting mixture was stirred vigorously at 60° C. for 1 h. The reaction mixture was washed with water, then the toluene layer was subjected to silica gel column chromatography to give the compound (2) 7.90 g as colorless crystal.(yield: 55%) m.p.:81–84° C.

$^1$H-NMR(CDCl$_3$) δ 1.25 (3H, t, J=7.2 Hz), 2.66 (2H, t, J=10.8 Hz), 3.00 (2H, t, J=10.8 Hz), 4.13 (2H, q, J=7.2 Hz), 5.16 (2H, s), 6.00 (1H, d, J=7.5 Hz), 6.31 (1H, t, J=7.5 Hz), 6.45 (1H, s), 7.12 (1H, s), 7.2–7.6 (6H, m).

Example 1
Process 2

To a solution of the compound (2) 1.00 g (3.1 mmol) in toluene (10 ml) was added benzoyl chloride 0.55 ml (4.7 mmol) at room temperature and the mixture was stirred at room temperature for 30 min and then at 80° C. for 1 h. The reaction mixture was washed with a saturated sodium bicarbonate solution and dried. The toluene solution was absorbed by silica gel and then the fraction eluted with toluene was recrystallized with ether to obtain the compound (3) 1.29 g colorless crystal. (yield: 98%) m.p.: 102–103° C.

$^1$H-NMR(CDCl$_3$) δ 1.15 (3H, t, J=7.2 Hz), 2.44 (2H, t, J=5.7 Hz), 2.58 (2H, t, J=5.7 Hz), 4.02 (2H, q, J=7.2 Hz), 5.21 (2H, s), 6.49 (1H, t, J=7.5 Hz), 6.59 (1H, s), 6.69 (1H, t, J=7.5 Hz), 7.3–7.6 (8H, m), 7.63 (2H, d, J=7.8 Hz), 9.18 (1H, d, J=6.9 Hz).

Example 1
Process 3

To a solution of aluminum chloride 1.87 g (14.0 mmol) in tetrahydrofuran (30 ml) was added sodium borohydride 2.73 g (72.0 mmol) in an ice bath, and the mixture was stirred at same temperature for 10 min. To it was added the compound (3) 3.00 g (7.0 mmol) and the mixture was stirred at room temperature for 2 h, and at 40° C. for 20 min. Then to the mixture was added ether (100 ml), and 2N aqueous sodium hydroxide solution (50 ml), and the resulting mixture was stirred vigorously. The ether layer was washed with saturated aqueous sodium chloride solution, dried, and evaporated to give the compound (4) 2.61 g as colorless oil. (yield: 100%) $^1$H-NMR(CDCl$_3$) δ 1.93 (2H, m), 2.39 (2H, t, J=7.29 Hz), 3.68 (2H, t, J=6.0 Hz), 4.25 (2H, s), 5.17 (2H, s), 6.02 (1H, d, J=7.4 Hz), 6.27 (1H, t, J=7.2 Hz), 6.59 (1H, s), 7.03 (2H, d, J=7.2 Hz), 7.20 (3H, m), 4.40 (4H, m), 7.42 (2H, d, J=7.2 Hz).

Example 1
Process 4

To a solution of the compound (4) 2.60 g (7.0 mmol) in tetrahydrofuran (30 ml) was added oxalyl chloride (5.0 ml) and the mixture was stirred at the same temperature for 1 h. To the reaction mixture was added 28% aqueous ammonia solution at −20° C. for 20 min, and the mixture was stirred at room temperature for 20 min. It was diluted with water and was extracted with ethyl acetate. The extracts were washed with water, dried, and evaporated. The residue was recrystallized from dichloromethane-ethanol to obtain the compound (5) 2.41 g as yellow crystal. (yield: 78%) m.p.: 171–173° C.

$^1$H-NMR(CDCl$_3$-CD$_3$OD) δ 1.84 (2H, m), 2.95 (2H, t, J=7.5 Hz), 3.59 (2H, t, J=6.3 Hz), 4.31 (2H, s), 5.25 (2H, s), 6.46 (1H, d, J=7.2 Hz), 6.55 (1H, dd, J=6.9, 7.0 Hz), 7.10–7.50 (11H, m).

Example 1
Process 5

A suspension of the compound (5) 1.51 g (3.41 mmol) and 10% palladium-carbon (200 mg) in tetrahydrofuran was stirred under hydrogen atmosphere. After filtration of the catalyst and evaporation of the filtrate, the residue was recrystallized from ethyl acetate to give the compound (6) 1.09 g. (yield: 91%) m.p.: 167–169° C.

$^1$H-NMR(CDCl$_3$-CD$_3$OD) δ 1.85 (2H, m), 2.92 (2H, m), 3.61 (2H, t, J=6.3 Hz), 4.25 (2H, s), 6.73 (1H, d, J=7.89 Hz), 6.82 (1H, t, J=7.8 Hz), 7.06 (2H, d, J=6.9 Hz), 7.30 (4H, m).

Example 1
Process 6

To a solution of the compound (6) 480 mg (1.36 mmol) in DMF (5 ml) were added methyl bromoacetate 0.41 ml (4.34 mmol), potassium iodide 100 mg, and powder potassium hydroxide 114 mg (2.04 mmol) at room temperature, and the mixture was stirred for 30 min. To it were added methyl bromoacetate 0.41 ml (4.34 mmol) and powder potassium hydroxide 114 mg (2.04 mmol), and the mixture was stirred for 30 min. The reaction mixture was poured into ethyl acetate, then the extract was washed with water, dried, and evaporated, and the residue was absorbed on silica gel, then the fraction eluted with ethyl acetate was recrystallized from ethyl acetate to give the compound (7) 350 mg. (yield: 60%) m.p.: 165–166° C.

$^1$H-NMR(CDCl$_3$) δ 1.85 (2H, m), 2.98 (2H, t, J=6.6 Hz), 3.40 (1H, brs), 3.59 (2H, t, J=5.4 Hz), 3.79 (3H, s), 4.26 (2H, s), 4.74 (2H, s), 5.75 (1H, brs), 6.31 (1H, t, J=7.8 Hz), 6.55 (1H, t, J=7.2 Hz), 6.65 (1H, brs), 7.04 (2H, d, J=6.6 Hz), 7.30 (3H, m), 7.34 (1H, d, J=6.9 Hz).

Example 1
Process 7

To a solution of the compound (7) 550 mg (1.30 mmol) in dichloromethane (7 ml) were added triphenylphosphine 407 mg (1.56 mmol) and NBS 278 mg (1.56 mmol) in an ice bath and the mixture was stirred at the same temperature for 1 h. The reaction mixture was absorbed on silica gel, the fraction eluted with chloroform/ethyl acetate=1/1 was recrystallized from ethyl acetate to give the compound (8) 520 mg. (yield: 83%) m.p.: 175–176° C.

$^1$H-NMR(CDCl$_3$) δ 2.20 (2H, m), 3.01 (2H, t, J=7.2 Hz), 3.46 (2H, t, J=6.3 Hz), 3.78 (3H, s), 4.29 (2H, s), 4.73 (2H, s), 5.70 (1H, brs), 6.28 (1H, d, J=7.8 Hz) 6.53 (1H, t, J=7.2), 6.80 (1H, brs), 7.07 (2H, d, J=6.6 Hz), 7.25 (3H, m), 7.36 (1H, d, J=7.2 Hz).

Example 1
Process 8

A solution of the compound (8) 510 mg (1.05 mmol) and triphenylphosphine 600 mg (2.25 mmol) in acetonitrile was refluxed for 6 h. The crystalline residue which was obtained by evaporation under reduced pressure was recrystallized from ethyl acetate to give the compound (9) 695 mg. (yield: 89%) decomp.p.:225–227° C.

$^1$H-NMR(CDCl$_3$) δ 1.95 (2H, m), 3.23 (2H, t, J=6.8 Hz), 3.66 (2H, m), 3.78 (3H, s), 4.41 (2H, s), 4.77 (2H, s), 5.85 (1H, brs), 6.28 (1H, d, J=7.8 Hz), 6.55 (1H, t, J=7.2 Hz), 6.83 (1H, brs), 7.03 (2H, m), 7.13 (3H, m), 7.40 (1H, d, J=7.2 Hz), 7.65 (15H, m).

Example 1
Process 9

To a suspension of the compound (9) 690 mg (0.92 mmol) in acetonitrile (10 ml) was added DBU 0.5 ml, and the mixture was stirred vigorously at room temperature for 20 h. After evaporation under reduced pressure, to the mixture were added ethyl acetate and 2N hydrochloric acid, and the resulting mixture was stirred. The ethyl acetate layer was washed with water, dried, evaporated, then the residue was absorbed on silica gel and fraction eluted with ethyl acetate was recrystallized to give the compound (I-1) 186 mg as yellow crystal. (yield: 52%) m.p.: 173–175° C.

$^1$H-NMR(CDCl$_3$) δ 2.39 (2H, m), 2.71 (2H, t, J=7.4 Hz), 3.79 (3H, s), 4.20 (2H, s), 4.70 (2H, s), 5.88 (1H, d, J=7.2 Hz), 6.25 (1H, t, J=7.2 Hz), 6.44 (1H, t, J=5.7 Hz), 7.09 (2H, d, J=7.2 Hz), 7.15 (4H, m).

Elementary Analysis (for C$_{23}$H$_{22}$N$_2$O$_4$) Calcd.:C, 70.75; H, 5.68; N, 7.17. Found:C, 70.53; H, 5.68; N, 7.11.

Example 2

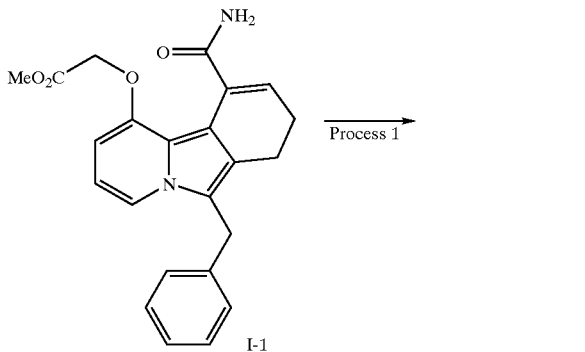

Process 1

To a solution of the compound (I-1) 20 mg (0.05 mmol) in tetrahydrofuran (0.5 ml) was added 1N aqueous sodium hydroxide solution (0.2 ml), and the mixture was stirred at room temperature for 10 min. After the precipitated crystal was filtered, washed with tetrahydrofuran, and dried, a solution of the crystal in water was stirred and adjusted with 1N hydrochloric acid to pH=4.0. The precipitated crystal was filtrated, washed with water, and then dried to give the compound (I-2) 15 mg. (yield: 78%) decomp.p.: 238–242° C.

$^1$H-NMR(CDCl$_3$-CD$_3$OD) δ 2.42 (2H, m), 2.74 (2H, t, J=7.2 Hz), 4.22 (2H, s), 4.70 (2H, s), 5.99 (1H, d, J=7.5 Hz), 6.30 (1H, t, J=7.2 Hz), 6.33 (1H, t, J=4.8 Hz), 7.10 (2H, d, J=6.6 Hz), 7.10–7.40 (4H, m).

Example 3

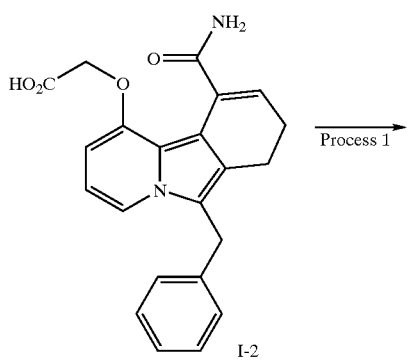

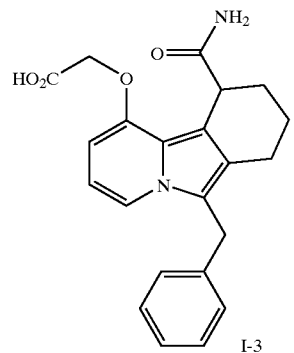

Process 1

A suspension of the compound (I-2) 10 mg (0.03 mmol) and 10% palladium-carbon (10 mg) in tetrahydrofuran (2 ml)-methanol (2 ml) was stirred under hydrogen atmosphere. After filtration of the catalyst and evaporation of the filtrate, the precipitated crystal was filtrated to give the compound (I-3) 7 mg. (yield: 70%) decomp.p: 240–245° C.

$^1$H-NMR(CDCl$_3$-CD$_3$OD) d 2.00 (3H, m), 2.25 (1H, m), 2.73 (1H, m), 2.86 (1H, m), 4.19 (2H, s), 4.31 (1H, m), 4.64(1H, s), 5.89 (1H, d, J=7.2 Hz), 6.28 (1H, t, J=6.9 Hz), 7.07 (2H, d, J=6.9 Hz), 7.10–7.30 (4H, m).

Example 4

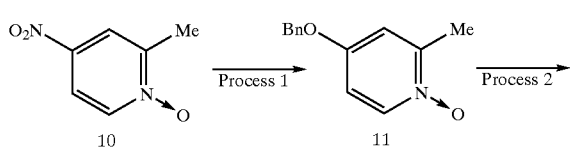

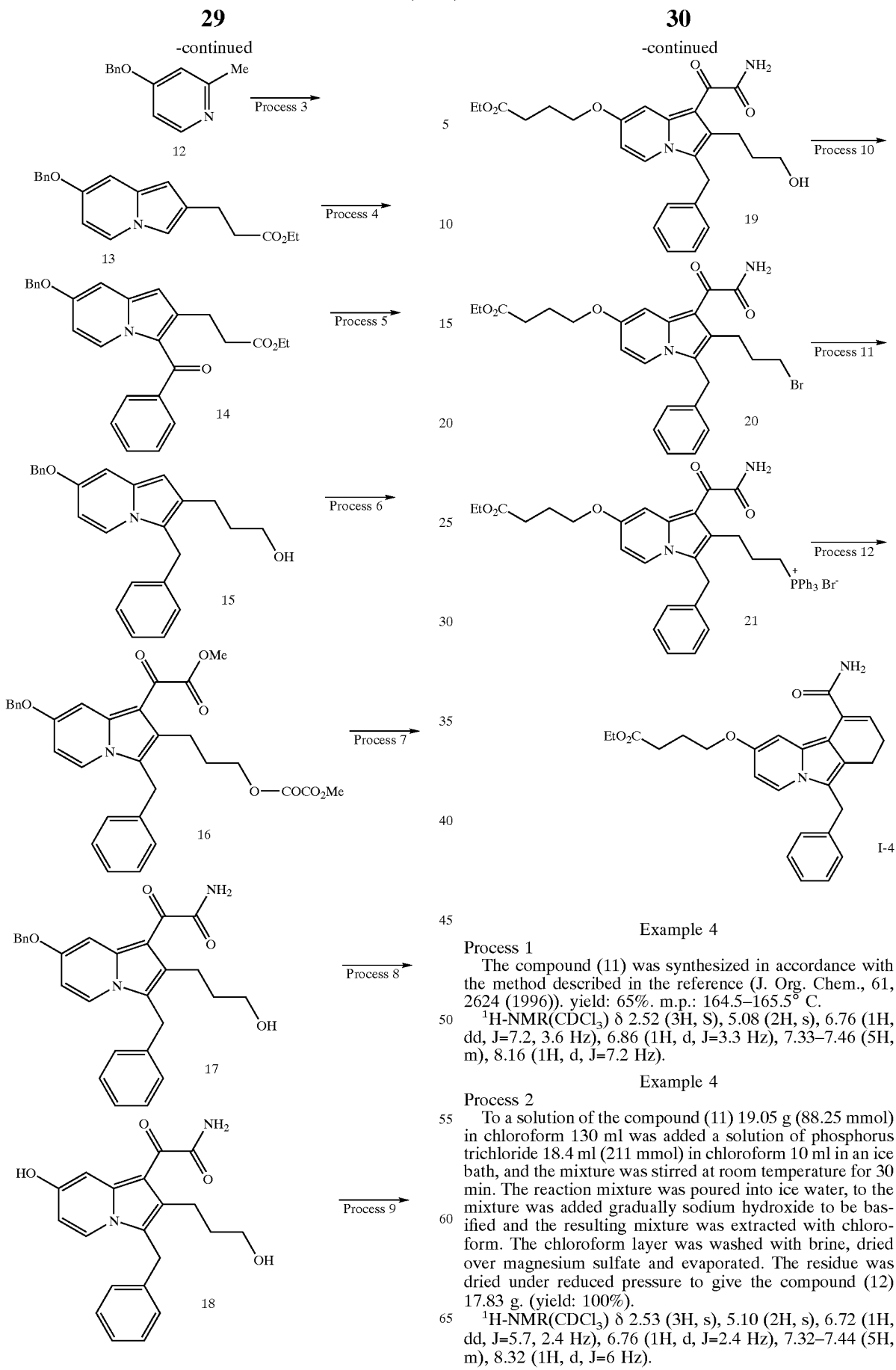

Example 4
Process 1
The compound (11) was synthesized in accordance with the method described in the reference (J. Org. Chem., 61, 2624 (1996)). yield: 65%. m.p.: 164.5–165.5° C.
$^1$H-NMR(CDCl$_3$) δ 2.52 (3H, S), 5.08 (2H, s), 6.76 (1H, dd, J=7.2, 3.6 Hz), 6.86 (1H, d, J=3.3 Hz), 7.33–7.46 (5H, m), 8.16 (1H, d, J=7.2 Hz).

Example 4
Process 2
To a solution of the compound (11) 19.05 g (88.25 mmol) in chloroform 130 ml was added a solution of phosphorus trichloride 18.4 ml (211 mmol) in chloroform 10 ml in an ice bath, and the mixture was stirred at room temperature for 30 min. The reaction mixture was poured into ice water, to the mixture was added gradually sodium hydroxide to be basified and the resulting mixture was extracted with chloroform. The chloroform layer was washed with brine, dried over magnesium sulfate and evaporated. The residue was dried under reduced pressure to give the compound (12) 17.83 g. (yield: 100%).
$^1$H-NMR(CDCl$_3$) δ 2.53 (3H, s), 5.10 (2H, s), 6.72 (1H, dd, J=5.7, 2.4 Hz), 6.76 (1H, d, J=2.4 Hz), 7.32–7.44 (5H, m), 8.32 (1H, d, J=6 Hz).

Example 4
Process 3

The compound (13) 6.68 g was obtained from the compound (12) 14.73 g in a manner similar to that described in Example 1—Process 1. (yield: 29%) m.p.: 84–87° C.

$^1$H-NMR(CDCl$_3$) δ 1.25 (3H, t, J=7.2 Hz), 2.64 (2H, t, J=7.7 Hz), 2.96 (2H, t, J=7.7 Hz), 4.14 (2H, q, J=7.2 Hz), 5.00 (2H, s), 6.04 (1H, s), 6.24 (1H, dd, J=7.2, 2.4 Hz), 6.59 (1H, d, J=2.4 Hz), 6.96 (1H, s), 7.29–7.46 (5H, m), 7.67 (1H, d, J=7.5 Hz).

Example 4
Process 4

To a solution of the compound (13) 6.66 g (20.59 mmol) in toluene 60 ml was added N-methylmorpholine 3.39 ml (30.83 mmol) and benzoyl chloride 3.58 ml (30.84 mmol) in an ice bath and the mixture was stirred at room temperature for 1.5 h. The reaction mixture was poured into water, and the resulting mixture was extracted with ethyl acetate. The extracts were washed with saturated aqueous sodium chloride solution, dried over magnesium sulfate and evaporated under reduced pressure. The residue was recrystallized from ethyl acetate-methanol-n-hexane to give the compound (14) 6.79 g as light yellow green needle crystal. (yield: 77%) m.p.: 137–138° C.

$^1$H-NMR(CDCl$_3$) d 1.16 (3H, t, J=7.2 Hz), 2.34–2.42 (2H, m), 2.47–2.55 (2H, m), 4.02 (2H, q, J=7.2 Hz), 5.121 (2H, s), 6.17 (1H, s), 6.63 (1H, dd, J=2.7, 7.8 Hz), 6.780 (1H, d, J=2.7 Hz), 7.32–7.53 (8H, m), 7.56–7.62 (2H, m), 9.66 (1H, d, J=7.8 Hz).

Example 4
Process 5

The compound (15) 5.49 g was obtained from the compound (14) 6.16 g in a manner similar to that described in Example 1—Process 3. (yield: 100%).

$^1$H-NMR(CDCl$_3$) δ 1.91 (2H, quint, J=6.9 Hz), 2.76 (2H, t, J=7.2 Hz), 3.68 (2H, t, J=5.7 Hz), 4.22 (2H, s), 5.00 (2H, s), 6.16 (1H, s), 6.19 (1H, dd, J=7.5, 2.7 Hz), 6.67 (1H, d, J=2.7 Hz), 7.03 (2H, d, J=7.2 Hz), 7.10–7.47 (9H,m).

Example 4
Process 6

To a solution of the compound (15) 215 mg (0.579 mmol) in tetrahydrofuran 3 ml were added N-methylmorpholine 0.134 ml (1.129 mmol) and methyl oxalyl chloride 0.112 ml (1.218 mmol) in an ice bath and the mixture was stirred at the same temperature for 40 min. The reaction mixture was poured into water, and the resulting mixture was extracted with ethyl acetate. The extracts were washed with saturated aqueous sodium chloride solution, dried over magnesium sulfate and evaporated under reduced pressure. The residue (292 mg) was purified with silica gel column chromatography (eluted with n-hexane/ethyl acetate=2/1 to 1/1) to give the compound (16) 106 mg as yellow foam. (yield: 34%).

$^1$H-NMR(CDCl$_3$) δ 2.00–2.12 (2H, m), 2.93 (2H, t, J=7.5 Hz), 3.86 (3H, s), 3.94 (3H, s), 4.21 (2H, s), 4.29 (2H, t, J=6.3 Hz), 5.13 (2H, s), 6.54 (1H, dd, J=7.5, 2.7 Hz), 7.03 (2H, d, J=6.3 Hz), 7.17–7.47 (8H, m), 7.55 (1H, d, J=7.5 Hz), 7.70 (1H,brs).

Example 4
Process 7

To a solution of the compound (16) 1.563 g (2.83 mmol) in tetrahydrofuran 20 ml was added 28% aqueous ammonia 50 ml and the solution was sealed and stirred at 70° C. for 6.5 h. The reaction mixture was poured into water, and the resulting mixture was extracted with ethyl acetate. The extracts were washed with brine, dried over magnesium sulfate and evaporated under reduced pressure. The residue (1.204 g) was purified with silica gel column chromatography (eluted with ethyl acetate to ethyl acetate/methanol=19/1) and successive recrystallization (ethyl acetate-ethyl ether) to give the compound (17) 758 mg as yellow needle crystal. (yield: 61%). m.p.: 157–158° C.

$^1$H-NMR(CDCl$_3$) δ 1.87 (2H, quint, J=6.6 Hz), 3.08 (2H, t, J=7.5 Hz), 3.63 (2H, t, J=5.7 Hz), 4.22 (2H, s), 5.12 (2H, s), 5.74 (1H, brs), 6.51 (1H, dd, J=7.5, 2.4 Hz), 6.87 (1H, brs), 7.05 (2H, d, J=6.6 Hz), 7.16–7.46 (8H, m), 7.52 (1H, d, J=7.5 Hz), 7.88 (1H, d, J=2.7 Hz).

Example 4
Process 8

The compound (18) 539 mg was obtained from the compound (17) 869 mg in a manner similar to that described in Example 1—Process 5. (yield: 78%) m.p.: 185–190° C.

$^1$H-NMR(DMSO-d$_6$) δ 1.70 (2H, quint, J=7 Hz), 2.86 (2H, t, J=7.5 Hz), 2.37–2.46 (2H), m), 4.25 (2H, s), 4.38 (1H, m), 6.52 (1H, dd, J=7.5, 2.7 Hz), 7.03 (2H, d, J=6.6 Hz), 7.15–7.32 (3H, m), 7.42 (1H, d, J=2.1 Hz), 7.49 (1H, s), 7.88 (1H, d, J=7.5 Hz), 7.96 (1H, s), 10.51 (1H, brs).

Example 4
Process 9

To a solution of the compound (18) 42 mg (0.119 mmol) in N,N-dimethylformamide 1 ml were added ethyl 4-bromobutyrate 34 μl (0.238 mmol) and 60% sodium hydride 4.8 mg (0.120 mmol) in an ice bath and the mixture was stirred at the same temperature for 1 h. Furthermore, to the reaction mixture were added ethyl 4-bromobutyrate 17 μl (0.119 mmol) and 60% sodium hydride 2.5 mg (0.063 mmol) and the mixture was stirred at the room temperature for 1 h. The reaction mixture was poured into water, and the resulting mixture was extracted with ethyl acetate. The extracts were washed with water and brine successively, dried over magnesium sulfate and evaporated under reduced pressure. The residue (71 mg) was purified with a precoated SiO$_2$ plate (Merck, 0.5 mm, 20*20 cm) to give the compound (19) 24 mg as light yellow crystal (43%). m.p.: 155–157° C.

$^1$H-NMR(CDCl$_3$) δ 1.25 (3H, t, J=7.2 Hz), 1.87 (2H, quint, J=6.7 Hz), 2.13 (2H, quint, J=6.7 Hz), 2.49 (2H, t, J=7.2 Hz), 3.08 (2H, t, J=7.2 Hz), 3.63 (2H, t, J=5.7 Hz), 4.08 (2H, t, J=6.6 Hz), 4.14 (2H, q, J=7.2 Hz), 4.13 (2H, s), 5.91 (1H, brs), 6.42 (1H, dd, J=7.5, 2.7 Hz), 6.95 (1H, brs).

Example 4
Process 10

The compound (20) 874 mg was obtained from the compound (19) 591 mg in a manner similar to that described in Example 1—Process 7.

$^1$H-NMR(CDCl$_3$) δ 1.25 (3H, t, J=7 Hz), 2.07–2.25 (4H, m), 2.49 (2H, t, J=7.2 Hz), 3.11 (2H, t, J=7.2 Hz), 2.45 (2H, t, J=6.6 Hz), 4.08 (2H, t, J=6.5 Hz), 4.14 (2H, q, J=7.2 Hz), 4.25 (2H, s), 5.84 (1H, brs), 6.42 (1H, dd, J=7.2,2.4 Hz), 6.93 (1H, brs), 7.07 (2H, d, J=6.3 Hz), 7.17–7.32 (3H, m), 7.78 (1H, d, J=2.4 Hz).

Example 4
Process 11

The compound (21) 622 mg was obtained from the compound (20) 874 mg in a manner similar to that described in Example 1—Process 8. (2 process yield from the compound (19): 62%).

$^1$H-NMR(CDCl$_3$) δ 1.25 (3H, t, J=7 Hz), 1.80–2.04 (2H, m), 2.12 (2H, quint, J=6.5 Hz), 2.48 (2H, t, J=7.2 Hz), 3.27

(2H, t, J=7.4 Hz), 3.66–3.84 (2H, m), 4.06 (2H, t, J=6 Hz), 4.14 (2H, q, J=7.2 Hz), 4.31 (2H, s), 6.24 (1H, brs), 6.42 (1H, dd, J=7.5, 2.4 Hz), 6.93–7.80 (23H, m).

Example 4

Process 12

The compound (I-4) 121 mg was obtained from the compound (21) 544 mg in a manner similar to that described in Example 1—Process 9. (yield: 41%) m.p.: 152–154° C.

$^1$H-NMR(CDCl$_3$) δ 1.25 (3H, t, J=7.2 Hz), 2.08 (2H, quint, J=6.7 Hz), 2.40–2.48 (2H, m), 2.47 (2H, t, J=7.2 Hz), 2.76 (2H, t, J=7.2 Hz), 3.96 (2H, t, J=6 Hz), 4.13 (2H, q, J=7.2 Hz), 4.17 (2H, s), 5.61 (1H, brs), 5.91 (1H, brs), 6.10 (1H, dd, J=7.5, 2.7 Hz), 6.34 (1H, t, J=4.8 Hz), 6.85 (1H, d, J=2.4 Hz), 7.08 (2H, d, J=6.6 Hz), 7.15–7.30 (3H, m), 7.38 (1H, d, J=7.5 Hz).

Example 5

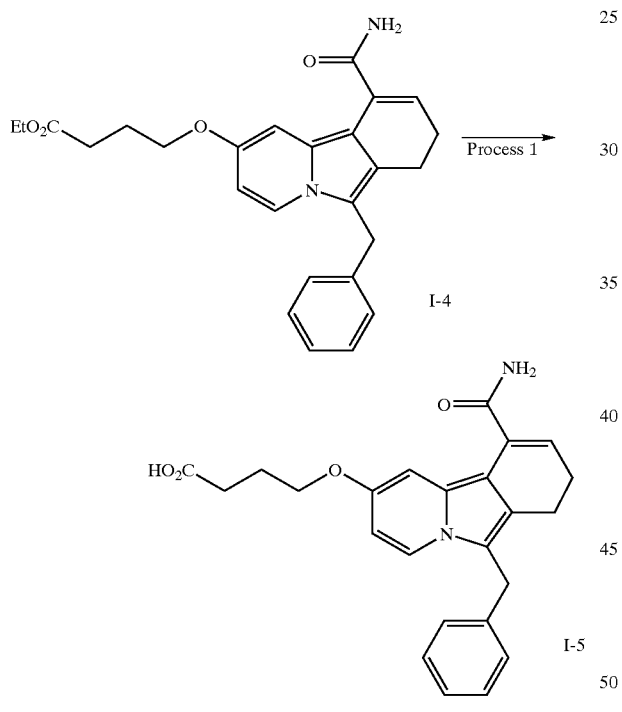

Example 5

Process 1

The compound (I-5) 42 mg was obtained from the compound (I-4) 54 mg in a manner similar to that described in Example 2—Process 1. (yield: 83%) m.p.: 180–183° C.

$^1$H-NMR(DMSO-d$_6$) δ 1.93 (2H, quint, J=6.9 Hz), 2.27–2.42 (4H, m), 2.72 (2H, t, J=7.5 Hz), 3.85 (2H, t, J=6 Hz), 4.19 (2H, s), 6.03 (1H, t, J=4.8 Hz), 6.20 (1H, dd, J=7.8, 2.7 Hz), 6.91 (1H, d, J=2.4 Hz), 7.08–7.30 (6H, m), 7.52 (1H, brs), 7.73 (1H, d, J=7.5 Hz), 12.14 (1H, brs).

Example 6

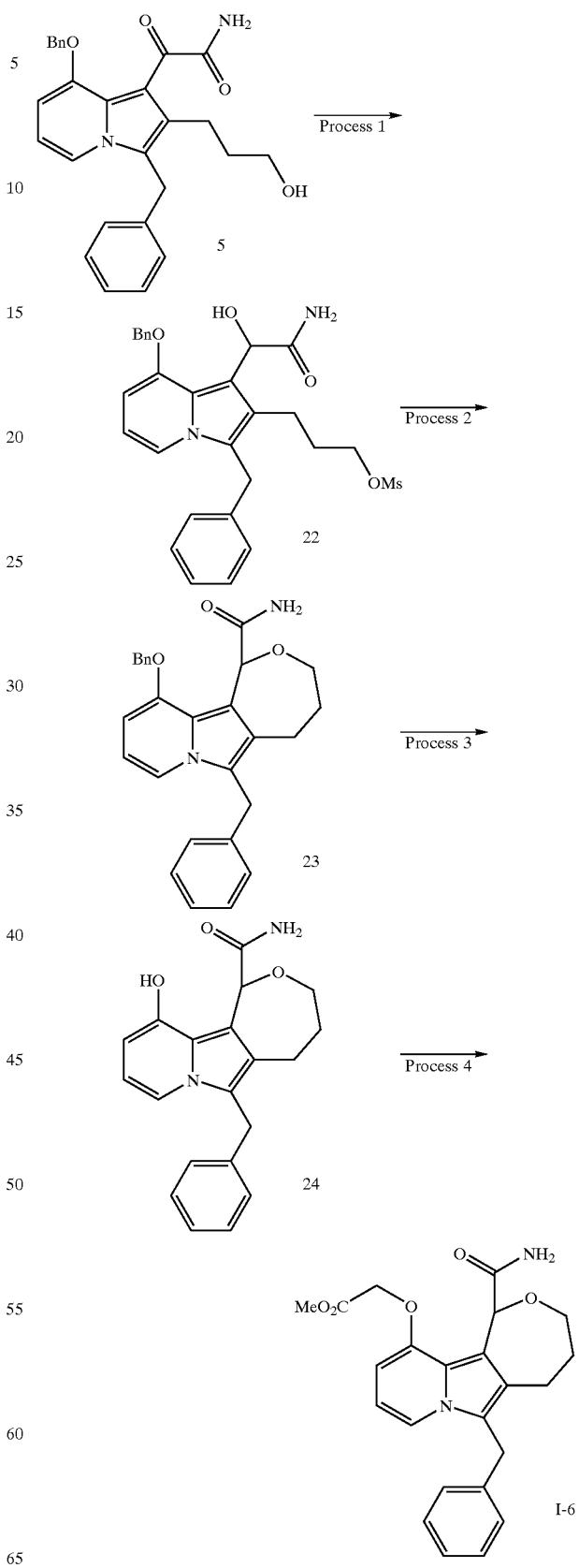

Example 6
Process 1

To a solution of the compound (5) 4.00 g (9.05 mmol) in dichloromethane 50 ml were added triethylamine 2.50 ml (18.1 mmol) and methanesulfonyl chloride 0.91 ml (11.8 mmol) in an ice bath, the mixture was stirred for 30 min. The mixture was diluted with ethyl acetate, and then the organic layer was washed with water, dried, and evaporated under reduced pressure. The residue was dissolved in a solvent mixed with tetrahydrofuran 50 ml and methanol 50 ml and then to the solution was added sodium borohydride 2.0 g at room temperature for 30 min. The reaction mixture was poured into ice water, and the resulting mixture was extracted with ethyl acetate. The extracts were washed with water, dried and evaporated under reduced pressure. The residue was recrystallized from ethyl acetate to give the compound (22) 3.62 g. (yield: 77%). m.p.: 140–141° C.

$^1$H-NMR(CDCl$_3$) δ 2.02 (2H, m), 2.85 (2H, m), 2.92 (3H, s), 3.68 (1H, d, J=7.5 Hz), 4.21 (3H, s), 4.23 (2H, s), 5.16 (1H, d, J=15.0 Hz), 5.18 (1H, d, J=15.0 Hz), 5.24 (1H, brs), 5.73 (1H d, J=7.5 Hz), 6.03 (1H, brs), 6.13 (1H, d, J=7.4 Hz), 6.31 (1H, t, J=7.4 Hz), 7.01 (2H, d, J=7.4 Hz), 7.10–7.50 (9H, m).

Example 6
Process 2

To a solution of the compound (22) 2.10 g (4.02 mmol) in a solvent mixed with N,N-dimethylformamide 20 ml and tetrahydrofuran 10 ml was added 60% sodium hydride 300 mg (5.00 mmol) under sonication at room temperature for 30 min and the mixture was stirred for 10 min under the same condition. The reaction mixture was poured into ethyl acetate-water, the ethyl acetate layer was washed with water and dried. The residue obtained by evaporation of the solvent under reduced pressure was absorbed on silica gel and the fraction eluted with toluene-ethyl acetate (4:1 to 1:2) was recrystallized to give the compound (23) 930 mg. (yield: 54%) m.p.: 201–203° C.

$^1$H-NMR(CDCl$_3$) δ 1.75 (1H, m), 2.04 (1H, m), 2.95 (2H, m), 4.07 (2H, m), 4.14 (1H, d, J=17.4 Hz), 4.26 (1H, d, J=17.4 Hz), 5.11 (2H, s), 5.45 (1H, brs), 6.06 (1H, d, J=7.2 Hz), 6.13 (1H, brs), 6.26 (1H, t, J=7.2 Hz), 6.35 (1H, s), 7.04 (2H, d, J=6.9 Hz), 7.10–7.50 (9H, m).

Example 6
Process 3

To a solution of the compound (23) 680 mg in ethyl acetate 80 ml was added 10% palladium-carbon 300 mg and the mixture was stirred under hydrogen atmosphere. After filtration of the catalyst and evaporation of the filtrate, the residue was recrystallized from toluene to give the compound (24) 296 mg. (yield: 57%) m.p.: 180–185° C.

$^1$H-NMR(CDCl$_3$) δ 1.70 (1H, m), 2.23 (1H m), 2.65 (1H, m), 3.10 (1H, m), 3.86 (1H, m), 4.12 (1H, m), 4.19 (2H, s), 5.90 (1H, brs), 5.98 (1H, s), 6.22 (1H, d, J=7.0 Hz), 6.31 (1H, t, J=7.2 Hz), 7.03 (2H, d, J=7.2 Hz), 7.10–7.30 (4H, m), 10.33 (1H, brs).

Example 6
Process 4

To a solution of the compound (24) 350 mg (1.08 mmol) in N,N-dimethylformamide 4 ml were added methyl bromoacetate 0.31 ml (3.27 mmol), potassium iodide 100 mg (0.60 mmol), and powder potassium hydroxide 63 mg (1.12 mmol), and the mixture was stirred at room temperature under sonication for 15 min. The reaction mixture was poured into water and the mixture was extracted with ethyl acetate. The extracts were washed with water and dried. The residue obtained by evaporation of the solvent under reduced pressure was purified with silica gel column chromatography (eluted with toluene-ethyl acetate (1:1 to 0:1) and successive recrystallization (ethyl acetate) to give the compound (I-6) 152 mg. (yield: 35%). m.p.: 182–183° C.

$^1$H-NMR(CDCl$_3$) δ 1.70 (1H, m), 2.10 (1H, m), 2.87 (1H, m), 3.15 (1H, m), 3.83 (3H, s), 4.03 (1H, m), 4.14 (1H, d, J=17.4 Hz), 4.19 (1H, m), 4.26 (1H, d, J=17.4 Hz), 4.67 (1H, d, J=15.6 Hz), 4.71 (1H, d, J=15.6 Hz), 5.40 (1H, brs), 5.89 (1H, d, J=7.2 Hz), 6.24 (1H, t, J=7.2 Hz), 6.43 (1H, s), 6.68 (1H, brs), 7.04 (2H, d, J=7.5 Hz), 7.10–7.30 (4H, m).

Example 7

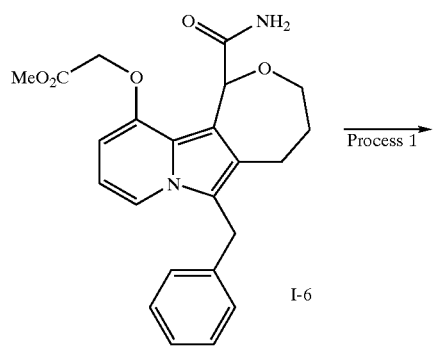

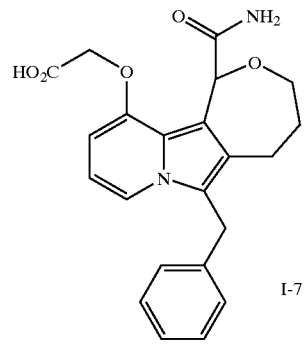

Example 7
Process 1

To a solution of the compound (I-6) 50 mg (0.12 mmol) in tetrahydrofuran 1 ml was added 1N aqueous sodium hydroxide solution 0.4 ml at room temperature, and the mixture was stirred for 20 min. After to the mixture was added 2N hydrochloric acid 0.2 ml, the resulting mixture was evaporated. To the residue was added water, the mixture was stirred, and then the precipitated crystal was filtrated to give the compound (I-7) 41 mg. (yield: 85%) m.p.: 175–179° C.

$^1$H-NMR(CDCl$_3$) δ 1.63 (1H, m), 2.22 (1H, m), 2.80 (1H, mn), 3.10 (1H, m), 3.87 (1H, m), 4.10 (1H, m), 4.17 (1H, d, J=16.5 Hz), 4.23 (1H, d, J=16.5 Hz), 4.60 (1H, d, J=14.0 Hz), 5.80 (1H, brs), 5.99 (1H, d, J=7.5 Hz), 6.11 (1H, s), 6.30 (1H, t, J=7.5 Hz), 7.02 (2H, d, J=6.9 Hz), 7.10–7.50 (5H, m).

Example 8

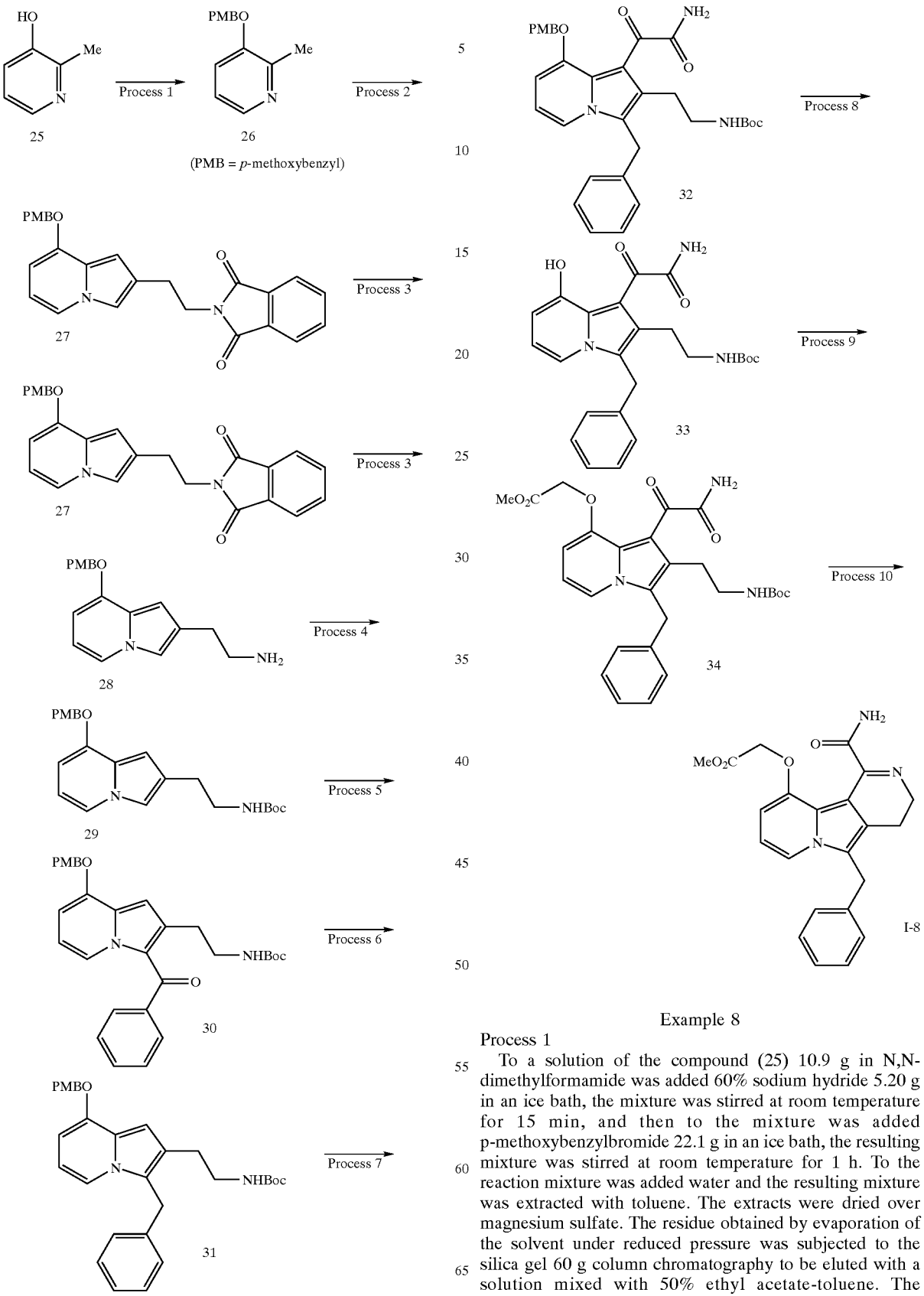

Example 8

Process 1

To a solution of the compound (25) 10.9 g in N,N-dimethylformamide was added 60% sodium hydride 5.20 g in an ice bath, the mixture was stirred at room temperature for 15 min, and then to the mixture was added p-methoxybenzylbromide 22.1 g in an ice bath, the resulting mixture was stirred at room temperature for 1 h. To the reaction mixture was added water and the resulting mixture was extracted with toluene. The extracts were dried over magnesium sulfate. The residue obtained by evaporation of the solvent under reduced pressure was subjected to the silica gel 60 g column chromatography to be eluted with a solution mixed with 50% ethyl acetate-toluene. The obtained crude crystal 15.97 g was recrystallized from ether-hexane to give the compound (26) 14.14 g as white crystal. (yield: 62%) m.p.: 74–76° C.

$^1$-NMR(CDCl$_3$) δ 2.51 (3H, s), 3.83 (3H, s), 5.01 (2H, s), 6.93 (2H, d), 7.02–7.15 (2H, m), 7.35 (2 H, d), 8.09 (1H, m).

Example 8
Process 2

A solution of the compound (26) 5.00 g and N-(4-bromo-3-oxobutyl)phthalimide 6.46 g in dichloromethane 15 ml was heated at 65° C. in an oil bath for 2 h evaporating dichloromethane. To the precipitate crystal were added dichloroethane 50 ml and DBU 3.98 g and the mixture was refluxed in an oil bath for 2 h. To the reaction mixture was added water and the resulting mixture was extracted with chloroform. The extracts were dried over magnesium sulfate. The residue obtained by evaporation of the solvent under reduced pressure was subjected to the silica gel 70 g column chromatography to be eluted with 3% acetonitrile-chloroform. To the obtained fraction was added isopropyl ether, the precipitate crystal was filtrate to obtain the compound (27) 6.41 g as yellow crystal (yield 69%). m.p.: 193–195° C.

$^1$H-NMR(CDCl$_3$) δ 3.05 (2H, t), 3.83 (3H, s), 3.96 (2H, t), 5.07 (2H, s), 6.01 (1H, d), 6.31 (1H, t), 6.51 (1H, brs), 6.93 (2H, d), 7.19 (1H, brs), 7.38 (2H, d), 7.51 (1H, d), 7.68–7.71 (2H, m), 7.82–7.85 (2H, m).

Example 8
Process 3

The mixture of the compound (27) 5.89 g and hydrazine hydrate 6.7 ml in ethanol 100 ml-tetrahydrofuran 100 ml was refluxed in an oil bath for 3 h. The precipitated crystal was filtrated and the filtrate was evaporated under reduced pressure. To the residue was added water, and the resulting mixture was extracted with chloroform. The extracts were dried over magnesium sulfate and the residue obtained by evaporation was subjected to the alumina 50 g column chromatography. The fraction eluted with 5% methanol-chloroform gave the compound (28) 4.20 g as colorless oil.

$^1$H-NMR(CDCl$_3$) δ 2.78 (2H, t), 2.98 (2H, t), 3.83 (3H, s), 5.09 (2H, s), 6.02 (1H, d), 6.32 (1H, t), 6.45 (1H, brs), 6.93 (2H, d), 7.14 (1H, s), 7.40 (2H, d), 7.52 (1H, d).

Example 8
Process 4

To a solution of the compound (28) 4.20 g in tetrahydrofuran 50 ml was added di-tert-butyl dicarbonate 3.16 g, and the mixture was stirred at room temperature for 1 h. Evaporation of the solvent under the reduced pressure and recrystallization by adding to the residue isopropyl ether obtained the compound (29) 5.03 g as white crystal. (yield: 92%) m.p.: 132–133° C.

$^1$H-NMR(CDCl$_3$) δ 1.43 (9H, s), 2.83 (2H, t), 3.41 (2H, m), 3.83 (3H, s), 4.60 (1H, brs), 5.09 (2H, s), 6.03 (1H, d), 6.34 (1H, t), 6.44 (1H, brs), 6.93 (2H, d), 7.12 (1H, brs), 7.40 (2H, d), 7.52 (1H, d).

Example 8
Process 5

A solution of the compound (29) 2.00 g, N-methylmorpholine and benzoyl chloride in dichloroethane 50 ml was refluxed for 2 h in an oil bath. To the reaction mixture was added water, and the resulting mixture was extracted with chloroform. The extracts were dried over magnesium sulfate and the residue obtained by evaporation was subjected to the silica gel 50 g column chromatography. The fraction 2.52 g eluted with 2.5% acetonitrile-chloroform was recrystallized from acetone-isopropyl ether to give the compound (30) 2.18 g as yellow crystal. (yield: 86%) m.p.: 135–137° C.

$^1$H-NMR(CDCl$_3$) δ 2.45 (2H, t), 3.19 (2H, m), 3.84 (3H, s), 4.33 (1H, brs), 5.14 (2H, s), 6.50 (1H, d), 6.61 (1H, s), 6.69 (1H, t), 6.95 (2H, d), 7.40 (2H, d), 7.43–7.63 (5H, m), 9.12 (1H, d).

Example 8
Process 6

To a solution prepared from aluminum chloride 533 mg and sodium borohydride 757 mg in tetrahydrofuran 30 ml was added a solution of the compound (30) 2.00 g in tetrahydrofuran 20 ml in an ice bath, the mixture was stirred at room temperature for 2.5 h. The reaction mixture was poured into ice water, and the resulting mixture was extracted with ether. The extracts were dried over magnesium sulfate and then evaporated. The solution of the residue in chloroform was subjected to the silica gel 50 g column chromatography. The fraction 1.49 g eluted with chloroform was recrystallized from acetone-isopropyl ether to give the compound (31) 1.30 g as white crystal. (yield: 67%) m.p.: 92–93° C.

$^1$H-NMR(CDCl$_3$) δ 1.40 (9H, s), 2.87 (2H, t), 3.40 (2H, m), 3.83 (3H, s), 4.23 (2H, s), 4.60 (1H, brs), 5.10 (2H, s), 6.04 (1H, d), 6.29 (1H, t), 6.55 (1H, brs), 6.94 (2H, d), 7.00–7.23 (6H, m), 7.41 (2H, d).

Example 8
Process 7

To a solution of the compound (31) 1.73 g, N-methylmorpholine 0.78 ml in dichloromethane 20 ml was added oxalyl chloride 1.55 ml in dichloromethane 20 ml at −16 to −18° C. and the mixture was stirred for 20 min. The reaction mixture was poured into a concentrated aqueous ammonia solution 15 ml, insoluble substances were filtrated and the filtrate was extracted with chloroform. The extracts were dried over magnesium sulfate, and subjected to the silica gel 20 g column chromatography. The fraction eluted with 20% acetonitrile-chloroform was recrystallized from isopropyl ether to obtain the compound (32) 1.76 g as yellow crystal. (yield: 89%) m.p.: 210–212° C. (decomposed).

$^1$H-NMR(DMSO-d$_6$) δ 1.33 (9H, s), 2.90 (2H, t), 3.14 (2H, m), 3.73 (3H, s), 4.29 (2H, s), 5.17 (2H, s), 6.44 (1H, d), 6.60 (1H, t), 6.84 (1H, brs), 6.89 (2H, d), 7.09–7.28 (6H, m), 7.45 (2H, d), 7.57 (1H, d), 7.67 (1H, brs).

Example 8
Process 8

A suspension of the compound (32) 1.55 g and 10% palladium-carbon 160 mg in a solution mixed with tetrahydrofuran 50 ml-methanol 50 ml was stirred for 5 h under hydrogen atmosphere. After filtration of the Pd-C and evaporation of the filtrate, the residue was subjected to the silica gel 12 g column chromatography. The fraction 1.14 g eluted with 20% acetonitrile-chloroform was recrystallized from acetone-isopropyl ether to obtain the compound (33) 0.823 g as yellow crystal. (yield: 68%) m.p.: 148–149° C.

$^1$H-NMR(DMSO-d$_6$) δ 1.35 (9H, s), 2.96 (2H, t), 3.16 (2H, m), 4.32 (2H, s), 6.68 (1H, d), 6.81 (1H, m), 6.95 (1H, t), 7.09–7.31 (5H, m), 7.65 (1H, d), 7.78 (1H, brs), 8.33 (1H, brs), 13.28 (1H, s).

Example 8
Process 9

A mixture of the compound (33) 650 mg, methyl bromoacetate 0.28 ml, potassium iodide 50 mg, potassium carbonate 206 mg in N,N-dimethylformamide 10 ml was stirred at room temperature for 6.5 h. The reaction mixture was poured into water and the precipitated crystal was filtrated. A solution of the crude product in chloroform was subjected to the silica gel 15 g column chromatography. The fraction 705 mg eluted with a solution mixed with 75% acetonitrile-chloroform was recrystallized from acetone-isopropyl ether to give the compound (34) 665 mg as yellow crystal. (yield: 88%) m.p.: 201–202° C.

$^1$H-NMR(CDCl$_3$) δ 1.38 (9H, s), 3.04 (2H, t), 3.41 (2H, m), 3.79 (3H, s), 4.26 (2H, s), 4.73 (2H, s), 5.19 (1H, brs), 5.50 (1H, brs), 6.29 (1H, d), 6.53 (1H, t), 6.80 (1H, brs), 7.05–7.28 (5H, m), 7.35 (1H, d).

Example 8
Process 10

To a solution of the compound (34) 250 mg in dichloromethane 10 ml was added trifluoroacetic acid 0.38 ml at room temperature. The solution was refluxed for 8 h in an oil bath. After to the reaction mixture were added ice and an aqueous ammonia solution to be basified, the resulting mixture was extracted with chloroform. After the extracts were dried over magnesium sulfate and subjected to the silica gel 5 g column chromatography. The fraction 236 mg eluted with a solution mixed with 10% methanol-chloroform was recrystallized from methanol-ethyl acetate to give the compound. (I-8) 165 mg as light yellow brown crystal. (yield: 86%) m.p.: 210–213° C. (decomposed).

$^1$H-NMR(DMSO-d$_6$) δ 2.65 (2H, t), 3.60 (2H, t), 3.70 (3H, s), 4.27 (2H, s), 4.77 (2H, s), 6.31 (1H, d), 6.57 (1H, t), 7.03 (1H, brs), 7.15–7.31 (5H, m), 7.38 (1H, brs), 7.69 (1H, d).

Example 9

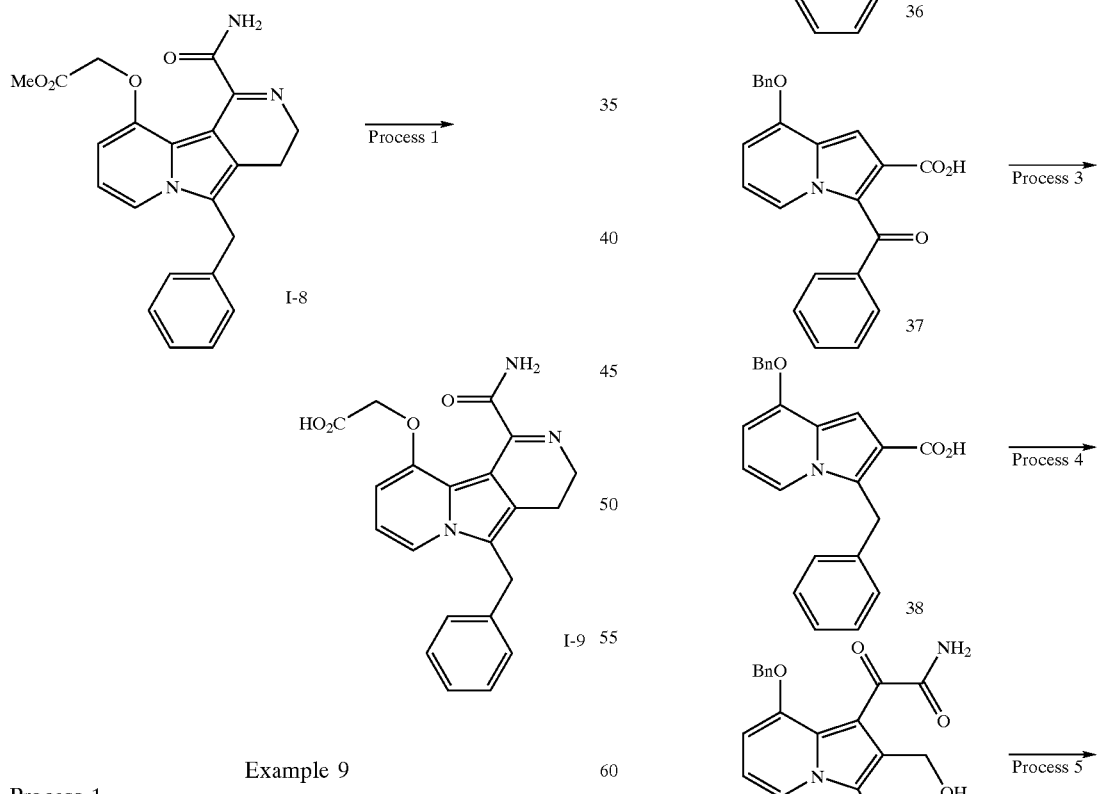

Example 9
Process 1

To a solution of the compound (I-8) 145 mg in methanol 15 ml was added a solution of sodium hydroxide 1.5 ml at room temperature, and the mixture was stirred for 75 min. To the residue obtained by evaporation of methanol under reduced pressure was added water, the resulting mixture was acidified with 1N hydrochloric acid 1.55 ml, and the precipitated crystal was filtrated. The crude crystal was recrystallized from methanol-water to give the compound (I-9) 121 mg as yellow crystal. (yield: 79%) m.p.: 196–198° C.

$^1$H-NMR(DMSO-d$_6$) δ 2.74 (2H, t), 3.63 (2H, t), 4.29 (2H, s), 4.60 (2H, s), 6.41 (1H, d), 6.71 (1H, t), 7.17–7.30 (5H, m), 7.39 (1H, brs), 7.67 (1H, brs), 7.75 (1H, d).

Example 10

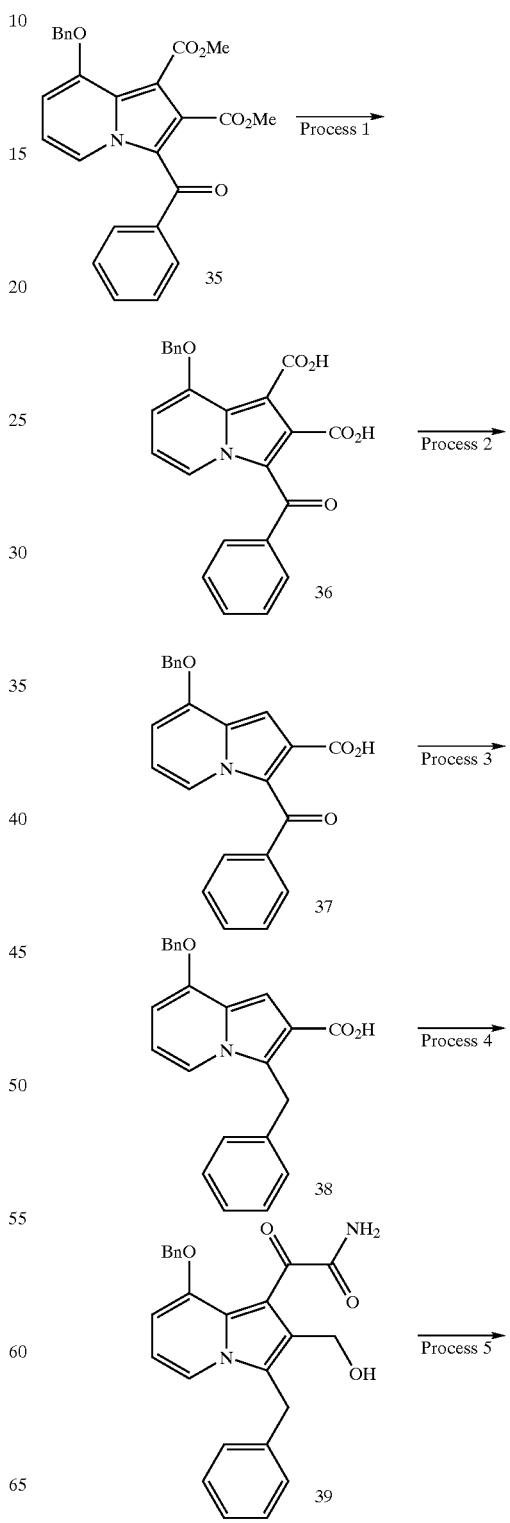

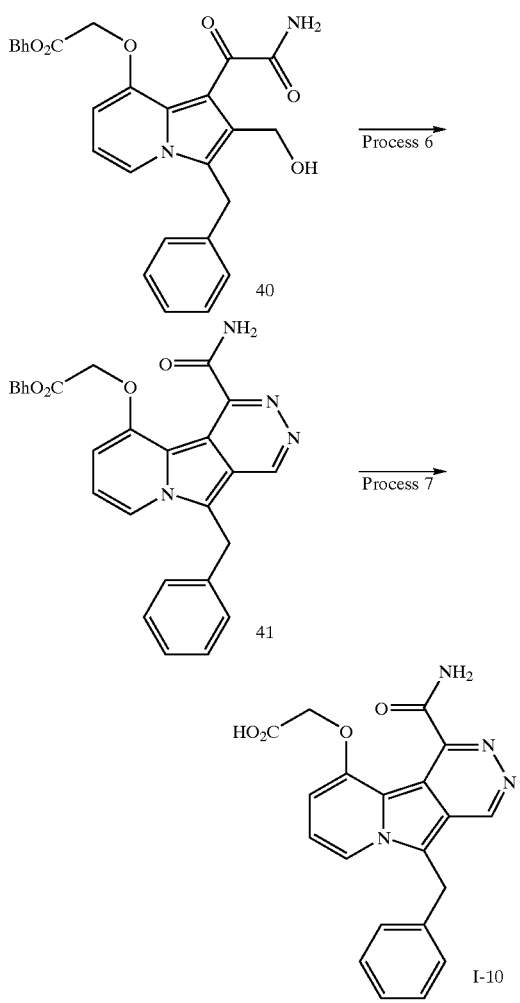

Example 10
Process 1

To a solution of the compound (35) 6.05 g (13.6 mmol) in methanol 50 ml was added an aqueous potassium hydroxide solution (85%, 4.5 g, 68 mmol) 20 ml, the mixture was refluxed for 4.5 h. After evaporation of methanol, the residue was acidified with 2N hydrochloric acid, and the resulting mixture was extracted with ethyl acetate. The extracts were dried over magnesium sulfate and evaporated to obtain the compound (36) 5.60 g as yellow powder. (yield: 99%).

$^1$H NMR (DMSO-$d_6$) δ 5.33(2H, s), 6.84(1H, d, J=7.2 Hz), 6.99(1H, t, J=7.2 Hz), 7.33–7.72(10H), 8.66(1H, d, J=7.2 Hz).

Example 10
Process 2

To a solution of the compound (36) 5.52 g (13.3 mmol) in N,N-dimethylformamide 25 ml was added p-toluenesufonic acid 253 mg (1.33 mmol). The mixture was stirred at 115° C. for 30 min, acidified with 2N hydrochloric acid, and extracted with ethyl acetate. The extracts were washed with brine, dried over sodium sulfate and then evaporated. The residue was purified with the silica gel column chromatography to give the compound (37) 4.85 as yellow powder. (yield: 98%).

$^1$H NMR (DMSO-$d_6$) δ 5.34(2H, s), 6.77(1H, d, J=7.5 Hz), 6.94(1H, s), 6.95(1H, t, J=7.5 Hz), 7.37–7.70(10H), 7.98(1H, t, J=7.5 Hz).

Example 10
Process 3

To a solution of the compound (37) 2.95 g (7.9 mmol) in tetrahydrofuran 20 ml was added sodium borohydride 1.5 g (40 mmol) and aluminum chloride 3,18 g (24 mmol) in an ice bath. The mixture was stirred at room temperature for 4 h and then refluxed for 3.5 h. To the mixture was added ice water, the resulting mixture was acidified with 2N hydrochloric acid, and extracted with ethyl acetate. The extracts were washed with brine, dried over sodium sulfate and then evaporated. The residue was purified with the silica gel column chromatography to give the compound (38) 1.37 g as light green powder. (yield: 48%).

$^1$H NMR (DMSO-$d_6$) δ 4.67(2H, s), 5.22(2H, s), 6.28(1H, d, J=7.2 Hz), 6.55(1H, t, J=7.2 Hz), 6.85(1H, s), 7.14–7.52 (10H), 7.63(1H, t, J=7.2 Hz).

Example 10
Process 4

To a solution of the compound (38) 1.37 g (3.8 mmol) in tetrahydrofuran 20 ml was added lithium aluminum hydride 1.16 g (31 mmol) and the mixture was stirred at 55° C. for 2 h. To the mixture was added ice water, the resulting mixture was acidified with 2N hydrochloric acid, and extracted with ethyl acetate. The extracts were dried over sodium sulfate and then evaporated to give the green oily substance. To a solution of the residue in tetrahydrofuran 20 ml was added oxalyl chloride 1.67 ml (19 mmol) in an ice bath. After stirring for 30 min, to the mixture was added a 28% aqueous ammonia solution 20 ml. The resulting mixture was stirred for further 1 h, and extracted with ethyl acetate. The extracts were dried over sodium sulfate and then evaporated. The residue was purified with the silica gel column chromatography to give the compound (39) 1.29 g as yellow powder. (yield: 82%).

$^1$H NMR (DMSO-$d_6$) δ 4.39(2H, s), 4.73(2H, d, J=5.7 Hz), 4.85(1H, t, J=5.7 Hz), 5.26(2H, s), 6.43(1H, d, J=7.2 Hz), 6.64(1H, t, J=7.2 Hz), 7.16–7.52(11H), 7.67(1H, d, J=7.2 Hz), 7.76(1H, brs).

Example 10
Process 5

To a solution of the compound (39) 600 mg (1.45 mmol) in tetrahydrofuran 20 ml was added 10% palladium-carbon 60 mg, the mixture was stirred at room temperature for 2 h under hydrogen atmosphere. The catalyst was filtrated and the solvent was evaporated. To a solution of the residue in N,N-dimethylformamide 10 ml were added potassium carbonate 600 mg (4.3 mmol), bezhydryl bromoacetate 530 mg (1.74 mmol), potassium iodide 25 mg (0.15 mmol), and the mixture was stirred at room temperature for 2 h. To the mixture was added ice water, the resulting mixture was acidified with 2N hydrochloric acid, and extracted with ethyl acetate. The extracts were washed with brine, dried over sodium sulfate and then evaporated. The residue was purified with the silica gel column chromatography to give the compound (40) 550 mg as yellow powder. (yield: 69%.).

$^1$H NMR (DMSO-$d_6$) δ 4.42(2H, s), 4.75(2H, d, J=5.7 Hz), 4.86(1H, t, J=5.7 Hz), 5.02(2H, s), 6.47(1H, d, J=7.5 Hz), 6.66(1H, t, J=7.5 Hz), 6.83(1H, s), 7.23–7.31(16H), 7.65(1H, brs), 7.74(1H, d, J=7.5 Hz).

Example 10
Process 6

To a solution of the compound (40) 372 mg (0.68 mmol) in dichloromethane 20 ml was added a solution of Dess-Martin reagent 316 mg (0.75 mmol) in dichloromethane 15 ml, and the mixture was stirred at room temperature for 5 min. The reaction mixture was washed with a 5% aqueous sodium hydrogen carbonate solution, dried over sodium sulfate and evaporated. To a solution of the residue in ethanol 20 ml was added hydrazine hydrate 50 mg (1.0 mmol), and the mixture was stirred at room temperature for 2 h. Evaporation of the solvent and purification with the silica gel column chromatography gave the compound (41) 45 mg as yellow powder. (yield; 12%).

$^1$H NMR (DMSO-d$_6$) δ 4.82(2H, s), 5.22(2H, s), 6.65(1H, d, J=7.5 Hz), 6.84(1H, s), 7.18–7.32(16H), 7.53(1H, brs), 7.87(1H, brs), 8.20(1H, d, J=7.5 Hz), 9.65(1H, s).

Example 10

Process 7

To a solution of the compound (41) 38 mg (0.07 mmol) in dichloromethane 1 ml were added anisole 0.1 ml and trifluoroacetic acid 0.1 ml at 010° C. After the mixture was stirred at room temperature for 15 min, it was evaporated and diluted with ether. The precipitated powder was filtrated, washed with ether and dried to give the compound (I-10) 26 mg as orange powder. (yield: 99%).

$^1$H NMR (DMSO-d$_6$) δ 4.93(2H, s), 5.05(2H, s), 7.20–7.33(6H), 7.62(1H, t, J=6.9 Hz), 8.28(1H, brs), 8.41 (1H, brs), 8.50(1H, d, J=6.9 Hz), 9.84(1H,s).

Example 11

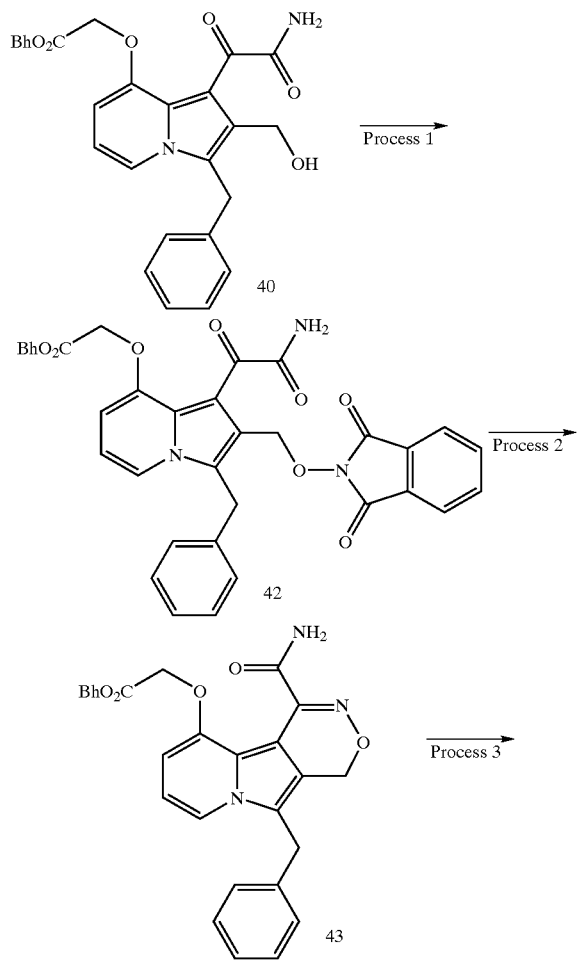

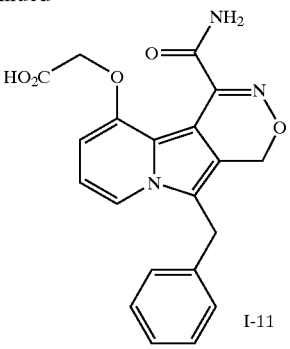

Example 11

Process 1

To a solution of the compound (40) 330 mg (0.60 mmol) in tetrahydrofuran 5 ml were added triphenylphosphine 174 mg (0.66 mmol), N-hydroxyphthalimide 103 mg (0.63 mmol), and diethyl azodicarboxylate 115 mg (0.66 mmol) in an ice bath, and the mixture was stirred for 30 min. After evaporation of the solvent, the residue was purified with silica gel chromatography to give the compound (42) 363 mg as yellow powder. (yield: 87%).

$^1$H NMR (DMSO-d$_6$) δ 4.59(2H, s), 5.01(2H, s), 5.53(2H, s), 6.46(1H, d, J=7.2 Hz), 6.69(1H, t, J=7.2 Hz), 6.83(1H, s), 7.15–7.34(16H), 7.59(1H, brs), 7.72(1H, d, J=7.2 Hz), 7.80–7.85(4H).

Example 11

Process 2

To a solution of the compound (42) 325 mg (0.47 mmol) in dichloromethane 6 ml was added N-methylhydrazine 22 mg (0.47 mmol) in an ice bath, and the mixture was stirred at room temperature for 30 min. Insoluble substances were filtrate and washed with dichloromethane. To the filtrate was added methanol 5 ml, and then the mixture was stirred at room temperature for 18 h. After evaporation of the solvent, the residue was diluted with ether, then the precipitated powder was filtrated, dried to give the compound (43) 193 mg as yellow powder. (yield: 74%).

$^1$H NMR (DMSO-d$_6$) δ 4.29(2H, s), 4.93(2H, s), 4.99(2H, s), 6.35(1h, d, J=7.2 Hz), 6.61(1H, t, J=7.2 Hz), 6.85(1H, s), 7.18–7.37(16H), 7.73(1H, brs), 7.78(1H, d, J=7.2 Hz).

Example 11

Process 3

To a solution of the compound (43) 50 mg (0.09 mmol) in dichloromethane 1 ml were added anisole 0.1 ml and trifluoroacetic acid 0.3 ml at 0° C. After the mixture was stirred at room temperature for 15 min, it was evaporated and diluted with ether. The precipitated powder was filtrated, washed with ether and dried to give the compound (I-11)16 mg as yellow powder. (yield: 47%).

$^1$H NMR (DMSO-d$_6$) δ 4.29(2H, s), 4.70(2H, s), 4.91(2H, s), 6.38(1H, d, J=7.2 Hz), 6.68(1H, t, J=7.2 Hz), 7.18–7.32 (5H), 7.39(1H, brs), 7.78(1H, d, J=7.2 Hz), 7.82(1H, brs).

The compounds (I-12) to (I-15) were synthesized by the same reactions described in the Examples 1 to Example 11. The physical data were shown in Tables 1 to 2.

TABLE 1

| Compound No. | R¹ | m.p. (° C.) | ¹H-NMR: δ CDCl₃ (R¹ = Me), CDCl₃—CD₃OD (R¹ = H) |
|---|---|---|---|
| I-12 | Me | 196–198 | 2.34–2.44(2H, m), 2.74(2H, t, J=7.4Hz), 3.79(3H, s), 4.24(2H, s), 4.71 (2H, s), 5.25–5.85(2H, brs), 5.90(1H, d, J=7.5Hz), 6.27(1H, t, J=7.2Hz), 6.45(1H, t, J=5.1Hz), 7.16(2H, d, J=8.4Hz), 7.27–7.58(8H, m) |
| I-13 | H | 224–227 | 2.30–2.54(2H, m), 2.68–2.88(2H, m), 4.28(2H, brs), 4.71(1H, s), 6.02(1H, m), 6.25–6.45(2H, m), 7.18(2H, d, J=7.8Hz), 7.28–7.60(8H, m) |

TABLE 2

| Compound No. | R¹ | m.p. (° C.) | ¹H-NMR: δ CDCl₃ (R¹ = Me), DMSO-d₆ (R¹ = H) |
|---|---|---|---|
| I-14 | Me | 218–220 | 2.74(1H, m), 2.93(1H, m), 3.82(3H, s), 4.14(1H, d, J=15.0Hz), 4.20(1H, d, J=15.0Hz), 4.18(2H, m), 4.67(1H, d, J=15.9Hz), 4.71(1H, d, J=15.6Hz), 5.52 (1H, brs), 5.86(1H, d, J=7.5Hz), 5.87 (1H, s), 6.29(1H, t, J=7.59Hz), 6.73 (1H, brs), 7.06(2H, d, J=7.3Hz), 7.20–7.40(4H, m) |
| I-15 | H | 242–243 (dec.) | 2.75(2H, m), 3.90(1H, m), 4.20(1H, m), 4.20(2H, s), 4.64(1H, d, J=16.8Hz), 4.67(1H, d, J=16.8Hz), 5.55(1H, s), 5.98(1H, d, J=7.2Hz), 6.37(1H, t, J=7.2Hz), 7.01(1H, brs), 7.10–7.30(6H, m), 7.54(1H, d, J=7.2Hz), 13.11(1H, brs) |

Test Example
Inhibition Test of Human Secretory Phospholipase A₂ Analytical Experiment In order to identify and evaluate an inhibitor of recombinant human secretory phospholipase A₂, the following chromogenic assay is utilized. The assay herein has been applied for high volume screening wherein 96 well microtiterplate is used. A general explanation for such assay is described in "Analysis of Human Synovial Fluid Phospholipase A₂ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis: the disclosure of which is incorporated herein for reference.

Reagents

Reaction Buffer $CaCl_2 \cdot 6H_2O$ (2.19 g/L)

KCl (7.455 g/L)

Bovine Serum Albumin (fatty acid free) (1 g/L) (Sigma A-7030)

Tris-HCl (3.94 g/L)

pH 7.5 (adjusted with NaOH)

Enzyme Buffer 0.05 M-AcONa 0.2 M-NaCl pH 4.5 (adjusted with acetic acid)

Enzyme Solution 1 mg of sPLA₂ is dissolved in 1 ml of an enzyme buffer. Thereafter, the solution is maintained at 4° C.

In the assay, 5 μl of the solution is diluted with 1995 μl of the reaction buffer to be used.

DTNB 198 mg of 5,5'-dithiobis-2-benzoic acid (manufactured by Wako Pure Chemicals) is dissolved in 100 ml of $H_2O$ pH 7.5 (adjusted with NaOH)

Substrate Solution 100 mg of racemic 1,2-bis(heptanoylthio)-1,2-dideoxy-sn-glycero-3-phospholylcholine is dissolved in 1 ml of chloroform.

Triton-X 100

624.9 mg of Triton-X 100 is dissolved in 100 ml of the reaction buffer.

Enzyme Reaction: for 1 plate of Microtiterplate 1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml of the reaction buffer and 0.46 ml of DTNB, and 0.18 ml each of the admixture is poured to wells of the 96 well microtiterplate.

2) 10 μl of a test compound (or solvent blank) are added in accordance with alignment of plates which has been previously set.

3) Incubation is effected at 40° C. for 15 minutes.

4) 20 μl of an enzyme solution (sPLA₂) which has been previously diluted (50 ng/well) are added to start reaction (40° C., 30 minutes).

5) Changes in absorbancy for 30 minutes are measured by a plate reader, and inhibition activity was calculated (OD: 405 nm).

6) IC₅₀ was determined by plotting log concentration with respect to inhibition values within 10% to 90% inhibiting range.

Results of the human secretory phospholipase A₂ inhibition test are shown in the following Table 3.

TABLE 3

| Compound No. | IC$_{50}$ ($\mu$M) | Compound No | IC$_{50}$ ($\mu$M) |
|---|---|---|---|
| I-2 | 0.008 | I-9 | 1.59 |
| I-3 | 0.021 | I-10 | 39.9 |
| I-4 | 0.175 | I-11 | 0.031 |
| I-5 | 0.049 | I-12 | 0.125 |
| I-6 | 7.50 | I-13 | 0.010 |
| I-7 | 0.269 | I-14 | 0.725 |
| I-8 | 21.1 | I-15 | 0.035 |

Formulation Example

It is to be noted that the following Formulation Examples 1 to 9 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

|  | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---|
| Active ingredient | 127 mg |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

INDUSTRIAL APPLICABILITY

The compounds according to the present invention have sPLA$_2$ inhibiting activity, so that the compounds of the invention inhibits sPLA$_2$-mediated fatty acid (such as arachidonic acid) release, whereby it is effective for treating inflammatory diseases and the like.

What is claimed is:

1. A compound represented by the formula (I):

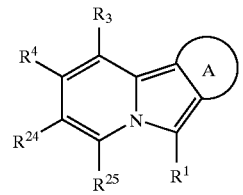

wherein $R^1$ is a group selected from (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, or (c) —(CH$_2$)$_m$—R$^5$ wherein m is an integer from 1 to 6, and $R^5$ is a group selected from the groups (a) and (b);

one of $R^3$ and $R^4$ is —(L$^2$)-(acidic group) wherein L$^2$ is represented by the formula:

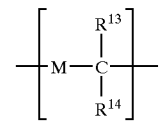

wherein M is —CH$_2$—, —O—, —N(R$^{15}$)—, or —S—; $R^{13}$ and $R^{14}$ are each independently a hydrogen atom, C1 to C10 alkyl, aryl, aralkyl, carboxy, or halogens, wherein $R^{15}$ is a hydrogen atom or C1 to C6 alkyl; and acidic group is represented by the formula:

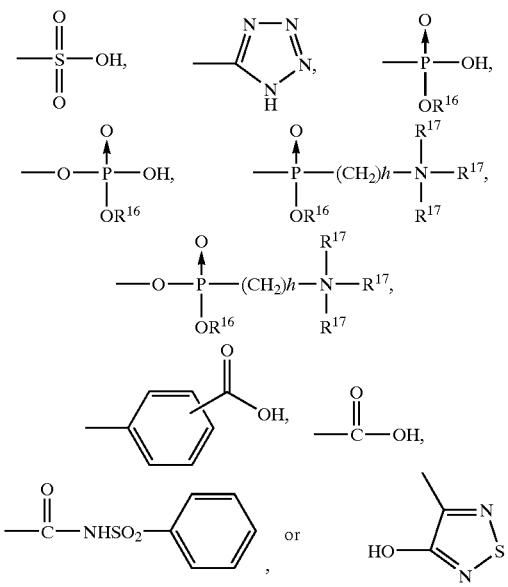

wherein $R^{16}$ is hydrogen atom, a metal, or C1 to C10 alkyl; $R^{17}$ is independently a hydrogen atom or C1 to C10 alkyl; h is an integer from 1 to 8 and the other is a hydrogen atom, A ring is a group represented by the formula:

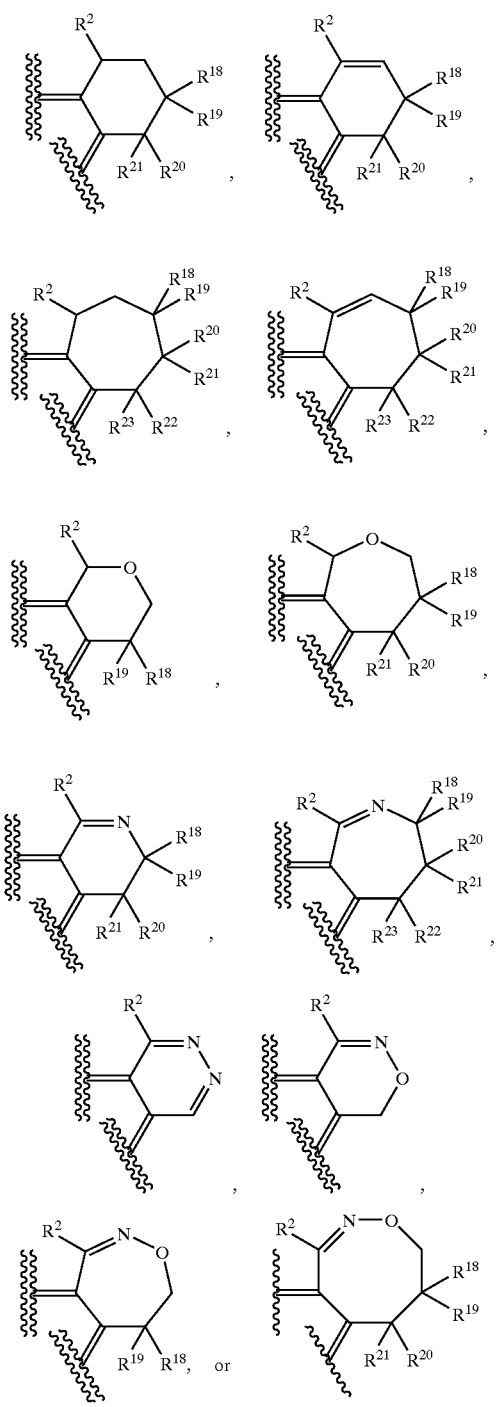

wherein $R^2$ is $CONH_2$ or $CONHNH_2$;
$R^{18}$, $R^{19}$, $R^{20}$, $R^{21}$, $R^{22}$, and $R^{23}$ are each independently a hydrogen atom, or lower alkyl;
$R^{24}$ and $R^{25}$ are each independently a hydrogen atom, C1 to C6 alkyl, aryl, a halogen or aralkyl;
its prodrug, their pharmaceutically acceptable salt, or hydrate thereof.

2. A compound represented by the formula (II):

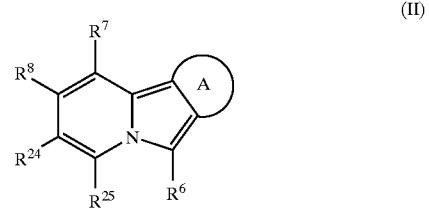

(II)

wherein $R^{24}$, $R^{25}$, and A ring are as defined above;
$R^6$ is $—(CH_2)_m—R^9$ wherein m is an integer from 1 to 6, and $R^9$ is (d) a group represented by the formula:

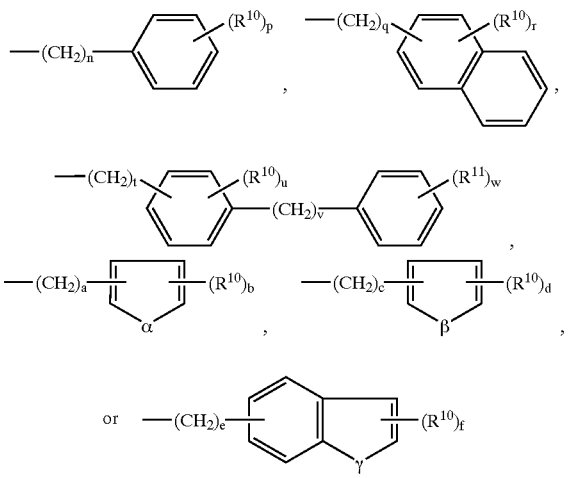

wherein a, c, e, n, q, t and v are each independently an integer from 0 to 2; $R^{10}$ and $R^{11}$ are each independently selected from a halogen, C1 to C10 alkyl, C1 to C10 alkyloxy, C1 to C10 alkylthio, optionally substituted phenyl, optionally substituted heteroaryl and C1 to C10 haloalkyl; α is an oxygen atom or a sulfur atom; β is $—CH_2—$ or $—(CH_2)_2—$; γ is an oxygen atom or a sulfur atom; b is an integer from 0 to 3, d is an integer from 0 to 4; f, p, and w are each independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen;
one of $R^7$ and $R^8$ is $—(L^3)—R^{12}$ wherein $L^3$ is represented by the formula:

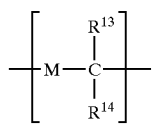

wherein M is $—CH_2—$, $—O—$, $—N(R^{15})—$, or $—S—$;
$R^{13}$ and $R^{14}$ are each independently a drogen atom, C1 to C10 alkyl, aryl, aralkyl, carboxy, or a halogen, and $R^{15}$ is a hydrogen atom or C1 to C6 alkyl; and $R^{12}$ is represented by the formula:

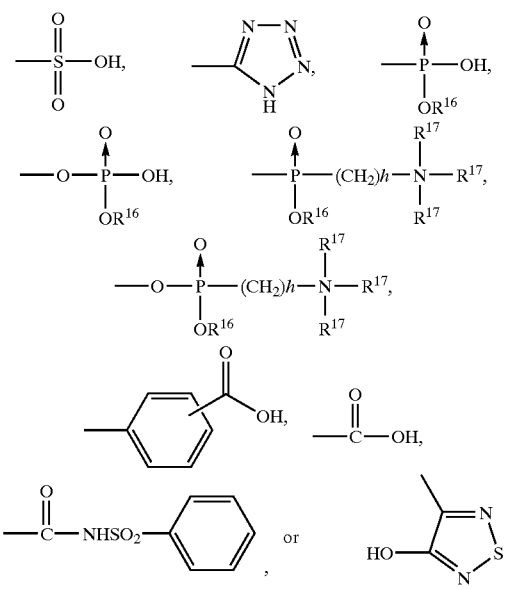

wherein $R^{16}$ is hydrogen atom, a metal, or C1 to C10 alkyl; $R^{17}$ is independently a hydrogen atom or C1 to C10 alkyl; h is an integer from 1 to 8;

its prodrug, their pharmaceutically acceptable salt, or hydrate thereof.

3. A compound, its prodrug, their pharmaceutically acceptable salt, or hydrate thereof as claimed in claim 1, wherein said $R^1$ is represented by the formula:

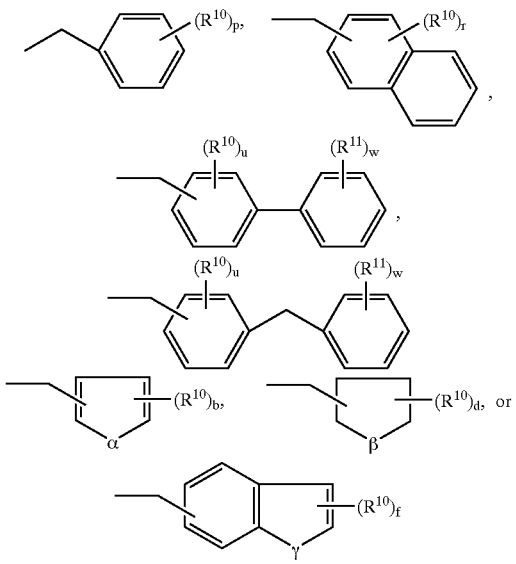

wherein $R^{10}$ and $R^{11}$ are each independently selected from a halogen, C1 to C10 alkyl, C1 to C10 alkyloxy, C1 to C10 alkylthio, optionally substituted phenyl, optionally substituted heteroaryl and C1 to C10 haloalkyl, $\alpha$ is an oxygen atom or a sulfur atom, $\beta$ is —$CH_2$— or —$(CH_2)_2$—; $\gamma$ is an oxygen atom or a sulfur atom; b is an integer from 0 to 3, d is an integer from 0 to 4; f, p, and w are each independently an integer from 0 to 5; r is an integer from 0 to 7, and u is an integer from 0 to 4.

4. A compound, its prodrug, their pharmaceutically acceptable salt, or hydrate thereof as claimed in claim 1, wherein said $R^1$ is represented by the formula:

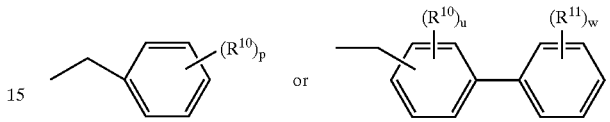

wherein $R^{10}$, $R^{11}$, p, u, and w are as defined above.

5. A compound, its prodrug, their pharmaceutically acceptable salt, or hydrate thereof as claimed in claim 1, wherein said $R^3$ and $R^7$ are —O—$(CH_2)_m$—COOH (m is as defined above).

6. A compound represented by the formula (III):

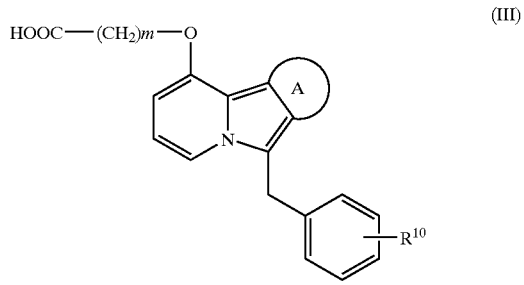

(III)

wherein $R^{10}$, A ring, and m are as defined above, its prodrug, their pharmaceutically acceptable salt, or hydrate thereof.

7. A compound, its prodrug, their pharmaceutically acceptable salt, or hydrate thereof as claimed in claim 1, wherein said $R^2$ is —$CONH_2$.

8. A compound, its prodrug, their pharmaceutically acceptable salt, or hydrate thereof as claimed in claim 1, wherein said $R^{18}$, $R^{19}$, $R^{20}$, $R^{21}$, $R^{22}$, and $R^{23}$ are hydrogen atoms.

9. A pharmaceutical composition containing a compound as claimed in claim 1 as an active ingredient.

10. A method for treating a mammal, including a human, to alleviate the pathological effects of a disease mediated by $sPLA_2$, which comprises administering to said mammal a compound as claimed in claim 1 in a pharmaceutically effective amount wherein the disease is selected from the group consisting of adult respiratory syndrome, pancreatitis, bronchial asthma, allergic rhinitis, chronic rheumatism, arteriosclerosis, cerebral infarction and psoriasis.

* * * * *